United States Patent
King et al.

(10) Patent No.: US 10,421,910 B2
(45) Date of Patent: Sep. 24, 2019

(54) SORBITOL, GLUCARIC ACID, AND GLUCONIC ACID BASED FLAME-RETARDANTS

(71) Applicant: International Business Machines Corporation, Armonk, NY (US)

(72) Inventors: Scott B. King, Rochester, MN (US); Brandon M. Kobilka, Tuscon, AZ (US); Joseph Kuczynski, North Port, FL (US); Jason T. Wertz, Pleasant Valley, NY (US)

(73) Assignee: International Business Machines Corporation, Armonk, NY (US)

( * ) Notice: Subject to any disclaimer, the term of this patent is extended or adjusted under 35 U.S.C. 154(b) by 156 days.

(21) Appl. No.: 15/678,813

(22) Filed: Aug. 16, 2017

(65) Prior Publication Data

US 2019/0055472 A1 Feb. 21, 2019

(51) Int. Cl.

| | | |
|---|---|---|
| *C09K 21/12* | (2006.01) | |
| *C07F 9/12* | (2006.01) | |
| *C07F 9/40* | (2006.01) | |
| *C08K 5/5357* | (2006.01) | |
| *C08K 5/523* | (2006.01) | |
| *C07F 9/655* | (2006.01) | |
| *C08K 5/5373* | (2006.01) | |
| *C08K 5/529* | (2006.01) | |
| *C08K 5/5333* | (2006.01) | |
| *C08K 5/521* | (2006.01) | |
| *C07F 9/113* | (2006.01) | |
| *H05K 1/03* | (2006.01) | |
| *C07F 9/6558* | (2006.01) | |
| *C07F 9/24* | (2006.01) | |
| *C07F 9/30* | (2006.01) | |

(52) U.S. Cl.
CPC ............. *C09K 21/12* (2013.01); *C07F 9/113* (2013.01); *C07F 9/12* (2013.01); *C07F 9/2458* (2013.01); *C07F 9/304* (2013.01); *C07F 9/4078* (2013.01); *C07F 9/4084* (2013.01); *C07F 9/65505* (2013.01); *C07F 9/65515* (2013.01); *C07F 9/65586* (2013.01); *C08K 5/521* (2013.01); *C08K 5/523* (2013.01); *C08K 5/529* (2013.01); *C08K 5/5333* (2013.01); *C08K 5/5357* (2013.01); *C08K 5/5373* (2013.01); *H05K 1/0326* (2013.01); *H05K 2201/012* (2013.01)

(58) Field of Classification Search
CPC ...... C08K 5/523; C08K 5/5357; C08K 5/529; C08K 5/5333; C08K 5/521; C09K 21/12; C07F 9/113; C07F 9/12; C07F 9/4078; C07F 9/4084; C07F 9/655505; H05K 1/0326; H05K 2201/012
See application file for complete search history.

(56) References Cited

U.S. PATENT DOCUMENTS

| | | |
|---|---|---|
| 2014/0058035 A1 | 2/2014 | Qi et al. |
| 2015/0275441 A1* | 10/2015 | Nordberg ................. C08K 5/49 404/75 |
| 2016/0083500 A1 | 3/2016 | Block et al. |
| 2016/0137676 A1 | 5/2016 | Rhudy et al. |
| 2016/0251485 A1 | 9/2016 | Boday et al. |

FOREIGN PATENT DOCUMENTS

WO 2006091894 A2 8/2006

OTHER PUBLICATIONS

Chatterjee et al., "Asymmetric synthesis of a 12-membered macrolactone core and a 6-epi analogue of amphidinolide W from 4-pentenoic acid," Tetrahedron: Asymmetry, Aug. 2012, vol. 23, Issues 15-16, pp. 1170-1185.

Das et al., "Facile total synthesis of (−)-(5R,6S)-6-acetoxy-5-hexadecanolide from carbohydrate, a mosquito oviposition attractant pheromone," Carbohydrate Research, Sep. 2012, vol. 358, pp. 7-11.

Dumbre et al., "Synthesis of Modified Peptidoglycan Precursor Analogues for the Inhibition of Glycosyltransferase," Journal of the American Chemical Society, 2012, 134 (22), pp. 9343-9351.

Hassan et al., "Formal synthesis of nanaomycin D via a Hauser-Kraus annulation using a chiral enone-lactone," Tetrahedron, Sep. 2015, vol. 71, Issue 39, pp. 7137-7143.

"Dimethyl Acetals," Organic Chemistry Portal, printed Aug. 3, 2017, pp. 1-2. http://www.organic-chemistry.org/protectivegroups/carbonyl/dimethylacetals.htm.

"Di-Acid Stereoisomers," SciFinder, pp. 1-2, © 2017 American Chemical Society (ACS).

"Mono-Acid Steroisomers," SciFinder, pp. 1-2, © 2017 American Chemical Society (ACS).

"Polyol Steroisomers," SciFinder, pp. 1-2, © 2017 American Chemical Society (ACS).

Chatterjee et al., "Asymmetric synthesis of a 12-membered macrolactone core and a 6-epi analogue of amphidinolide W from 4-pentenoic acid," Tetrahedron: Asymmetry, Aug. 2012, vol. 23, Issues 15-16, pp. 1170-1185. (Abstract).

Das et al., "Facile total synthesis of (−)-(5R,6S)-6-acetoxy-5-hexadecanolide from carbohydrate, a mosquito oviposition attractant pheromone," Carbohydrate Research, Sep. 2012, vol. 358, pp. 7-11. (Abstract).

(Continued)

*Primary Examiner* — Christopher M Rodd

(74) *Attorney, Agent, or Firm* — James L. Olsen

(57) ABSTRACT

A flame-retardant sugar derivative, a process for forming a flame-retardant sugar derivative, and an article of manufacture comprising a flame-retardant sugar derivative are disclosed. The flame-retardant sugar derivative can be synthesized from sorbitol, gluconic acid, or glucaric acid obtained from a bio-based source, and can have at least one phosphoryl or phosphonyl moiety. The process for forming the flame-retardant sugar derivative can include reacting sorbitol, gluconic acid, or glucaric acid and a flame-retardant phosphorus-based molecule to form the flame-retardant sugar derivative.

20 Claims, 32 Drawing Sheets

(56) References Cited

OTHER PUBLICATIONS

Dumbre et al., "Synthesis of Modified Peptidoglycan Precursor Analogues for the Inhibition of Glycosyltransferase," Journal of the American Chemical Society, 2012, 134 (22), pp. 9343-9351. (Abstract).
Hassan et al., "Formal synthesis of nanaomycin D via a Hauser-Kraus annulation using a chiral enone-lactone," Tetrahedron, Sep. 2015, vol. 71, Issue 39, pp. 7137-7143. (Abstract).

* cited by examiner

E: Thiol-ene with 360, UV

A: DPCPa or DPCPo, DMAP, DCM, reflux
B: Deprotection
C: Functional Linker FR on Hydroxyls A: DPCPa or DPCPo, DMAP, DCM, reflux
E: Functional Linker FR on Carboxylic-Acids

SORBITOL, GLUCARIC ACID, AND GLUCONIC ACID BASED FLAME-RETARDANTS

BACKGROUND

The present disclosure relates generally to the field of bio-renewable compounds, and more particularly, to bio-renewable flame retardants.

Bio-based, sustainable compounds can be used in the syntheses of substances that previously required petroleum-based raw materials. For example, bio-based compounds can be used in polymers, flame retardants, cross-linkers, etc. There are numerous strategies for efficiently and inexpensively producing bio-based compounds on an industrial scale. These strategies can include fermentation technologies, membrane technologies, and genetic engineering, to name a few.

SUMMARY

Embodiments of the present disclosure include a flame-retardant sugar derivative, a process for forming a flame-retardant sugar derivative, and an article of manufacture comprising a flame-retardant sugar derivative. The flame-retardant sugar derivative can be synthesized from sorbitol, gluconic acid, or glucaric acid obtained from a bio-based source, and can have at least one phosphoryl or phosphonyl moiety. The process for forming the flame-retardant sugar derivative can include reacting sorbitol, gluconic acid, or glucaric acid and a flame-retardant phosphorus-based molecule to form the flame-retardant sugar derivative.

The above summary is not intended to describe each illustrated embodiment or every implementation of the present disclosure.

BRIEF DESCRIPTION OF THE DRAWINGS

The drawings included in the present disclosure are incorporated into, and form part of, the specification. They illustrate embodiments of the present disclosure and, along with the description, serve to explain the principles of the disclosure. The drawings are only illustrative of typical embodiments and do not limit the disclosure.

Figure 1:
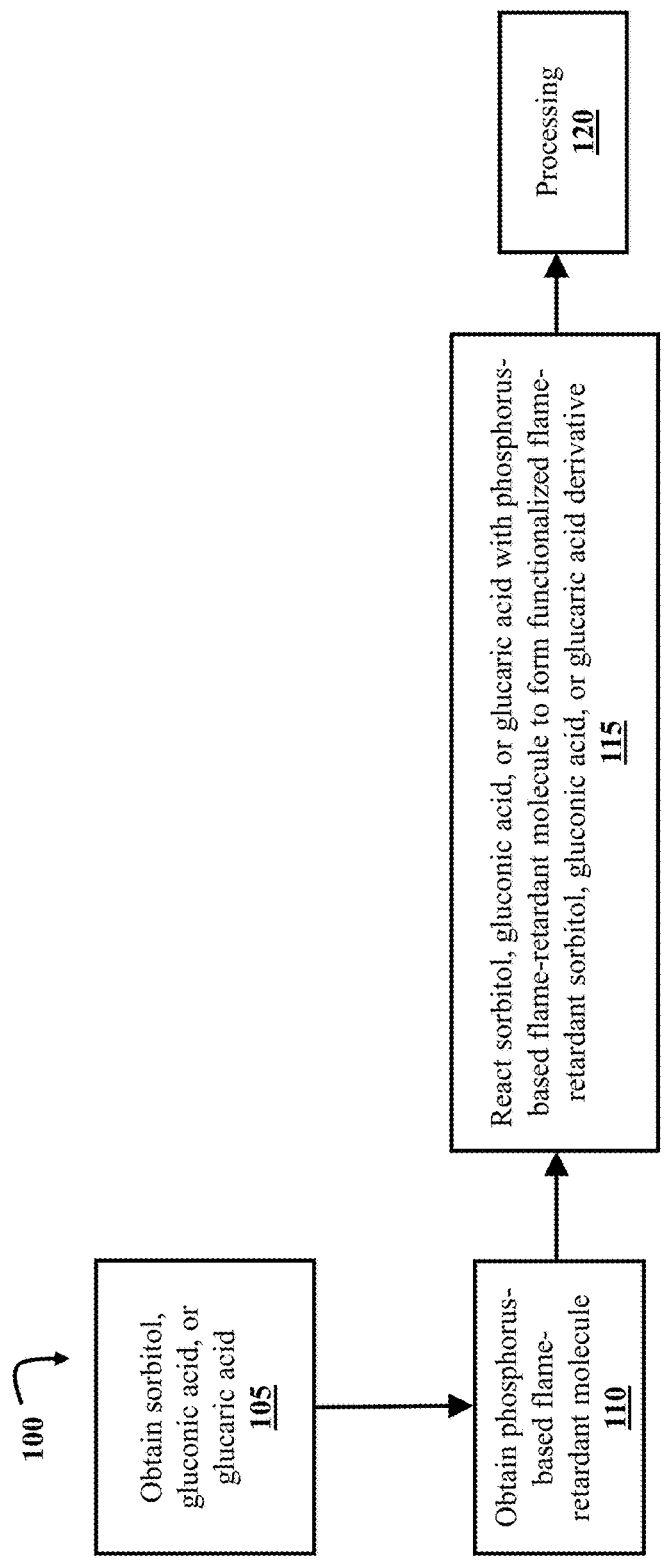
FIG. 1 is a flow diagram illustrating a process of forming a flame-retardant polymer containing sorbitol-derived, gluconic acid-derived, or glucaric acid-derived molecules, in accordance with embodiments of the present disclosure.

While the embodiments described herein are amenable to various modifications and alternative forms, specifics thereof have been shown by way of example in the drawings and will be described in detail. It should be understood, however, that the particular embodiments described are not to be taken in a limiting sense. On the contrary, the intention is to cover all modifications, equivalents, and alternatives falling within the spirit and scope of the invention.

DETAILED DESCRIPTION

Aspects of the present disclosure relate generally to the field of bio-renewable compounds, and more particularly, to bio-renewable flame retardants. While the present disclosure is not necessarily limited to such applications, various aspects of the disclosure may be appreciated through a discussion of various examples using this context.

Bio-based compounds are increasingly being used in the syntheses of substances that previously required petroleum-based raw materials. One benefit of bio-based compounds is that they are from renewable resources. Therefore, these compounds have applications in sustainable, or "green," materials. Sustainable materials are becoming more and more prevalent, due to the rising costs of fossil fuels and increasing environmental regulatory controls. Advances in biotechnology have provided numerous strategies for efficiently and inexpensively producing bio-based compounds on an industrial scale. For example, these strategies can be found in fermentation technologies, membrane technologies, and genetic engineering. Two approaches that can use biotechnologies are plant-based and microorganism-based approaches. Plant-based approaches can involve obtaining a material directly from a plant, or growing plant tissues or cells that can produce bio-based compounds from various substrates using their own biosynthetic pathways. Microorganism-based approaches involve using native or genetically modified fungi, yeast, or bacteria to produce a desired compound from a structurally similar substrate.

Bio-based compounds can be used in a variety of applications. For example, bio-based compounds can be used in polymers, flame retardants, and cross-linkers. In some examples, bio-based polymers and petroleum-based polymers are blended to form a polymer composite. However, polymers can also be entirely bio-based, or produced from a combination of bio- and petroleum-based monomers. Bio-based compounds can impart flame-retardant properties to bio- and petroleum-based polymers. For example, flame-retardant molecules or cross-linkers can be incorporated into polymers. Additionally, flame-retardant monomers can be polymerized to form flame-retardant polymers.

Sorbitol ((2S,3R,4R,5R) Hexane-1,3,4,5,6-hexol, or glucitol) and its oxidized carboxylic acid forms, gluconic acid (one carboxylic acid) and glucaric acid (two carboxylic acids), are examples of bio-based compounds that have applications as a component of various polymers, resins, and monomers. Sorbitol is a sugar alcohol obtained by the reduction of glucose. Specifically, the aldehyde group in glucose can be reduced into a hydroxyl group to form sorbitol. Sorbitol is commonly made from glucose obtained from corn, barely, potatoes, rice, wheat and various fruits (e.g., apples, pears, peaches, prunes). Gluconic acid and glucaric acid can be obtained by oxidizing sorbitol or sugars, such as glucose, or may alternatively be obtained from fruits or honey.

According to embodiments of the present disclosure, sorbitol and its oxidized carboxylic acid forms (e.g., gluconic acid and glucaric acid) may be used as a precursor for various flame-retardant molecules (e.g., small molecules or functionalized molecules). The sorbitol-derived, gluconic acid-derived, and/or glucaric acid-derived flame-retardant molecules can be added to polymers, fabrics, resins, or other materials during blending, curing, foaming, extrusion, or other processing techniques. In addition to directly adding the sorbitol-derived, gluconic acid-derived, and/or glucaric acid-derived flame retardants into the materials during processing, the flame retardants may be integrated into microcapsules. The sorbitol-derived, gluconic acid-derived, and glucaric acid-derived cross-linkers may each have six functional R groups, which may bind to resins and/or polymers. The addition of these cross-linkers causes a resin or polymer to be flame-retardant. The sorbitol-derived, gluconic acid-derived, and glucaric acid-derived molecules may be mono-functional, difunctional, trifunctional, tetrafunctional, pentafunctional, or hexafunctional, depending on the number of functional R groups bound to the molecules.

FIG. 1 is a flow diagram illustrating a process 100 of forming a flame-retardant polymer containing sorbitol-derived, gluconic acid-derived, or glucaric acid-derived molecules, in accordance with embodiments of the present disclosure. Process 100 may begin by obtaining sorbitol, gluconic acid, and/or glucaric acid at step 105. These molecules may be naturally obtained (e.g., from fruits, honey, and the like) or synthesized from other biomolecules (e.g., glucose and fructose). At step 110, phosphorus-based flame-retardant molecules may be obtained. The phosphorus-based flame-retardant molecules may have either a phosphoryl or a phosphonyl moiety (collectively referred to as an FR group) with an attached R functional group or phenyl (Ph) group. The R groups that are attached to the FR groups can vary, as is discussed in greater detail below. The phosphorus-based flame-retardant molecules can be phosphate- or phosphonate-based flame-retardant molecules. The structures and syntheses of phosphorus-based flame-retardant molecules are discussed in greater detail with regard to FIGS. 2-3D.

After the sorbitol, gluconic acid, or glucaric acid molecules and phosphorus-based flame-retardant molecules are obtained at steps 105 and 110, respectively, the sorbitol, gluconic acid, or glucaric acid molecules may be reacted with the phosphorus-based flame-retardant molecules to form functionalized flame-retardant sorbitol, gluconic acid, or glucaric acid derivatives at step 115. The structures and syntheses of the functionalized flame-retardant molecules are discussed in greater detail with regard to FIGS. 5-9.

The structure of the functionalized flame-retardant molecule formed at operation 115 is determined by the precursor (e.g., sorbitol, gluconic acid, or glucaric acid) and phosphorus-based flame-retardant molecule used in the reaction. The phosphorus-based flame-retardant molecule reacts with a hydroxyl group and/or carboxylic acid group on the sorbitol, gluconic acid, or glucaric acid molecule to provide an FR group with an attached R functional group. Examples of R groups can include phenyl substituents, epoxy functional groups, allyl functional groups, propylene carbonate substituents, hydroxyl-functionalized thioether substituents, amino-functionalized thioether substituents, carboxylic acid-functionalized thioether substituents, etc. The syntheses and structures of the functionalized flame-retardant sorbitol-derived, gluconic acid-derived, or glucaric acid-derived molecules are discussed in greater detail with regard to FIGS. 5-9.

The sorbitol, gluconic acid, or glucaric acid derived flame-retardant may be processed at step 120. The nature of the processing may depend on the identity of the flame-retardant derivative. Processing 120 may include chemically reacting a functionalized flame-retardant sorbitol, gluconic acid, or glucaric acid derivative with a polymer, forming a bond between the flame-retardant and the polymer. In some embodiments, processing 120 may include adding a flame-retardant sorbitol, gluconic acid, or glucaric acid small molecule to a polymer (e.g., during blending, extrusion, etc.). Examples of polymers include epoxies, polyhydroxyurethanes, polycarbonates, polyesters, polyacrylates, polyimides, polyamides, polyureas, poly(vinyl-esters), etc. The materials for these polymers can come from petroleum-based sources, bio-based sources, or a combination of petroleum- and bio-based sources. Further, in some embodiments, the flame-retardant molecules can be used in non-polymeric applications, such as resins for varnishes and adhesives. Flame retardant sorbitol, gluconic acid, or glucaric acid derived monomers may be polymerized in a reaction with a base and/or second monomer. Additionally, in some embodiments, the monomers may be polymerized in a reaction with a Ziegler-Natta catalyst. Polymerizations reactions with the flame-retardant monomers are discussed in greater detail with regard to FIG. 9.

Figure 2:
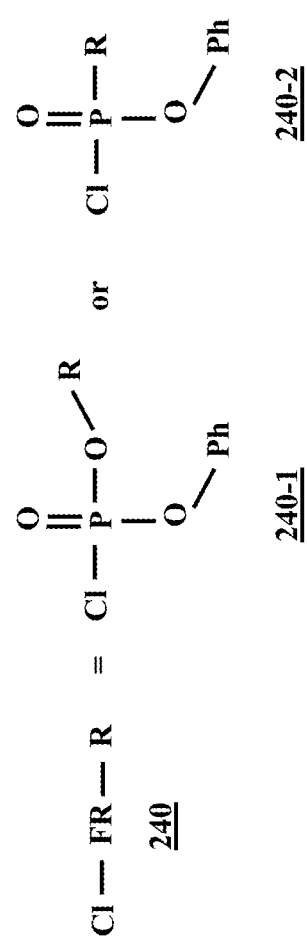
FIG. 2 is a diagrammatic representation of the molecular structures of generic phosphorus-based flame-retardant molecules, in accordance with embodiments of the present disclosure.
Figure 2:
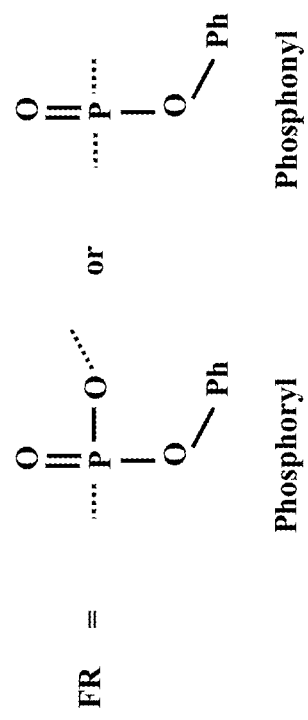
Figure 2:
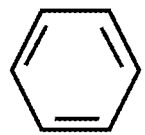

FIG. 2 is a diagrammatic representation of the molecular structures 202 of generic phosphorus-based flame-retardant molecules 240, in accordance with embodiments of the present disclosure. Each phosphorus-based flame-retardant molecule 240 is either a phosphate-based flame-retardant molecule 240-1 or a phosphonate-based flame-retardant molecule 240-2. Herein, phosphoryl and phosphonyl moieties are replaced by the abbreviation "FR" in order to simplify illustrations of the molecular structures. Each phosphorus-based flame-retardant molecule 240 has a phenyl (Ph) substituent and an R group. In some examples, the R group can bind to a resin.

The identities of the R groups bound to the phosphorus-based flame-retardant molecules 240 vary, and are discussed in greater detail with respect to FIGS. 3A-3D. Additionally, in some embodiments, the phenyl group is replaced by an alkyl substituent (e.g., methyl, ethyl, propyl, isopropyl, etc.). The syntheses of the phosphorus-based flame-retardant molecules 240 are discussed with regard to FIGS. 3A-3D.

Figure 3A:
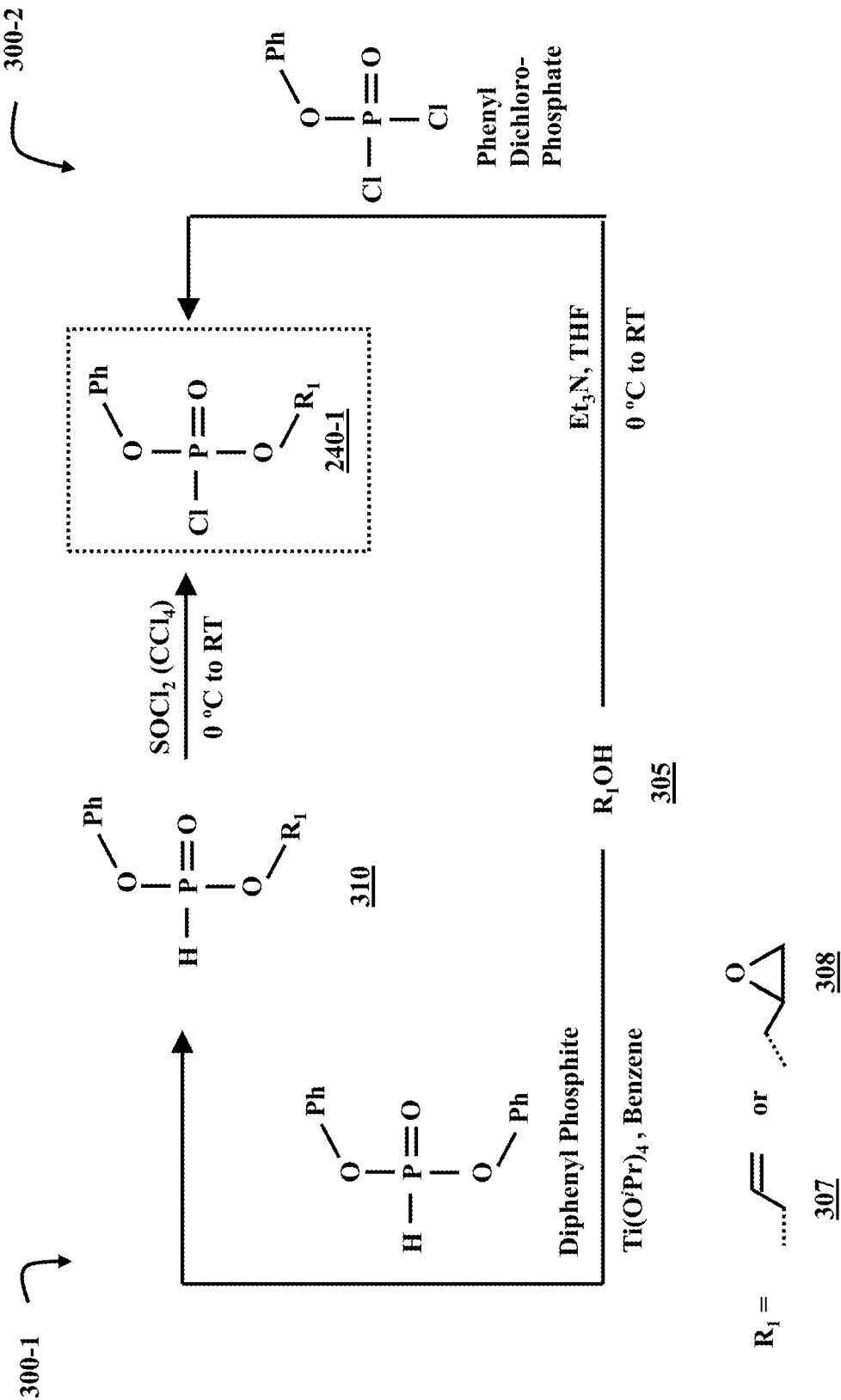
FIG. 3A is a chemical reaction diagram illustrating two processes of synthesizing phosphate-based flame-retardant molecules, in accordance with embodiments of the present disclosure.

FIG. 3A is a chemical reaction diagram illustrating two processes 300-1 and 300-2 of synthesizing the phosphate-based flame-retardant molecule 240-1, in accordance with embodiments of the present disclosure. In both processes 300-1 and 300-2, an alcohol 305 is a starting material for the phosphate-based flame-retardant molecule 240-1. The alcohol 305 has either an allyl $R_1$ group 307 or an epoxide $R_1$ group 308. It should be noted that, though an allyl group 307 with a single methylene spacer group is illustrated here, other alcohols with allylic chains of varying lengths (e.g., one to twelve methylene spacer groups) could be used. Additionally, alcohols with acrylate substituents are used in some embodiments.

In process 300-1, the alcohol 305 is reacted with diphenyl phosphite and titanium isopropoxide (Ti(O$^i$Pr)$_4$) in benzene to produce a precursor 310 to the phosphate-based flame-retardant molecule 240-1. In this pseudo-transesterification reaction, the precursor 310 is formed when a phenyl (Ph) substituent on diphenyl phosphite is replaced by an allyl 307 or epoxide 308 $R_1$ group from the alcohol 305. The precursor 310 is then reacted with thionyl chloride (SOCl$_2$) and carbon tetrachloride (CCl$_4$) over a range of 0° C. to room temperature (RT), forming the phosphate-based flame-retardant molecule 240-1.

In process 300-2, the alcohol 305 is reacted with phenyl dichlorophosphate in a tetrahydrofuran (THF) solution containing triethyl amine (Et$_3$N). This process is carried out over a range of 0° C. to room temperature (RT). A chloride on the phenyl dichlorophosphate is replaced by the alcohol 305, forming the phosphate-based flame-retardant molecule 240-1 with an allyl 307 or epoxide 308 $R_1$ group.

Figure 3B:
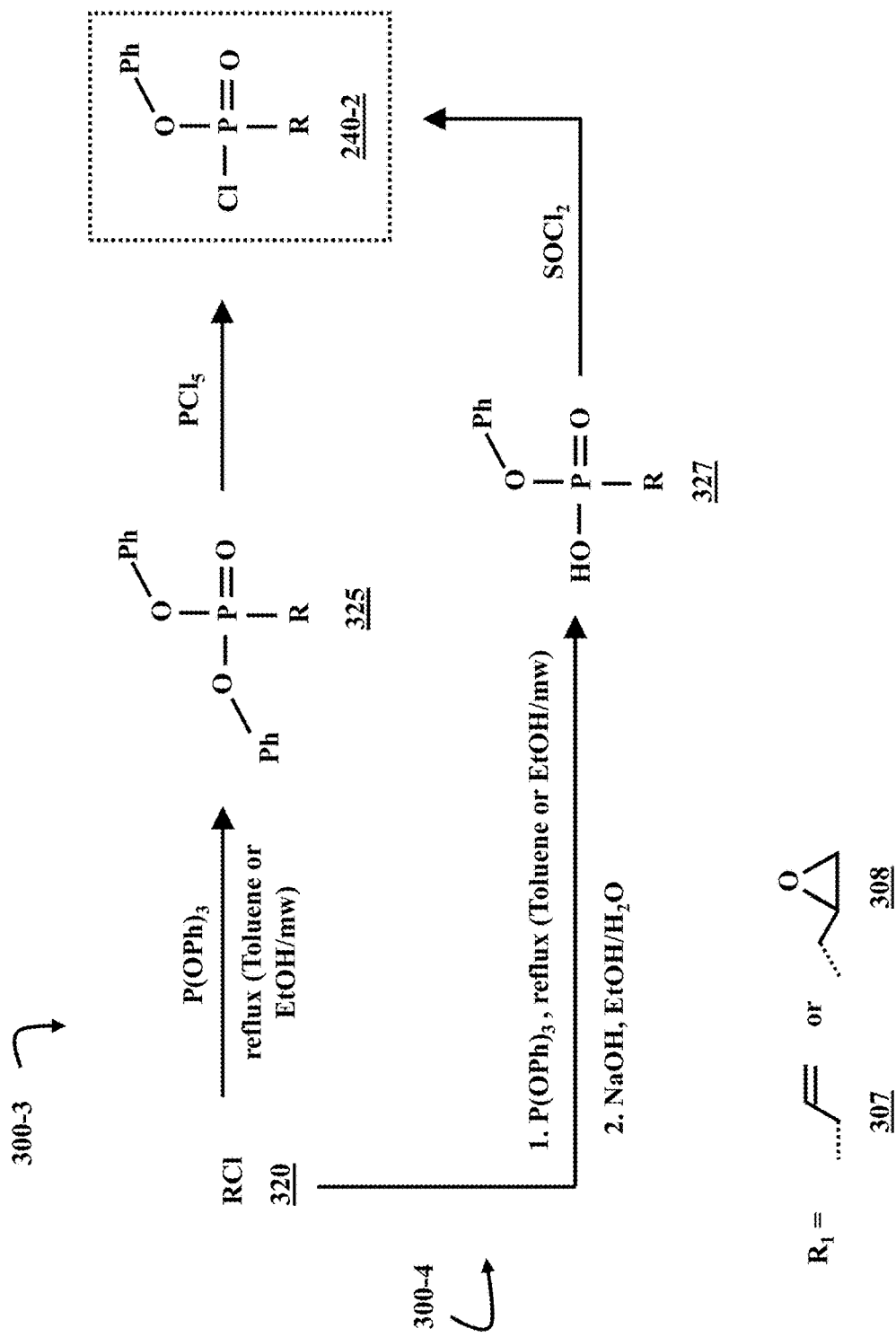
FIG. 3B is a chemical reaction diagram illustrating two processes of synthesizing phosphonate-based flame-retardant molecules, in accordance with embodiments of the present disclosure.

FIG. 3B is a chemical reaction diagram illustrating two processes 300-3 and 300-4 of synthesizing the phosphonate-based flame-retardant molecule 240-2, in accordance with embodiments of the present disclosure. In both processes 300-3 and 300-4, an organochloride 320 is a starting material for the phosphonate-based flame-retardant molecule 240-2. The organochloride has either an allyl $R_1$ group 307 or an epoxide $R_1$ group 308. It should be noted that, as in the case of the alcohol 305, other organochlorides with allylic chains of varying lengths (e.g., one to twelve methylene spacer groups) could be used. Additionally, organochlorides with acrylate substituents are used in some embodiments.

In process 300-3, the organochloride 320 is reacted with triphenyl phosphite (P(OPh)$_3$). The mixture is heated, either by refluxing in toluene or microwaving (mw) in ethanol (EtOH), producing a phosphonyl ester precursor 325 to the phosphonate-based flame-retardant molecule 240-2. The phosphonyl ester precursor 325 is reacted with phosphorus pentachloride (PCl$_5$) to form the phosphonate-based flame-retardant molecule 240-2 with an allyl 307 or epoxide 308 $R_1$ group.

In process 300-4, a mixture of the organochloride 320 and triphenyl phosphite (P(OPh)$_3$) is heated, either by refluxing in toluene or microwaving (mw) in ethanol (EtOH), forming a phenylphosphinic acid precursor 327 to the phosphonate-based flame-retardant molecule 240-2. The reaction is then quenched by raising the pH of the solution. In this prophetic example, an ethanol (EtOH)/water ($H_2O$) solution of sodium hydroxide (NaOH) is added to the reaction mixture. However, in some embodiments, bases other than sodium hydroxide, such as potassium hydroxide or lithium hydroxide, are used to quench the reaction. When the reaction has been quenched, thionyl chloride ($SOCl_2$) is added to the phenylphosphinic acid precursor 327, producing the phosphonate-based flame-retardant molecule 240-2 with an allyl 307 or epoxide 308 $R_1$ group.

Figure 3C:
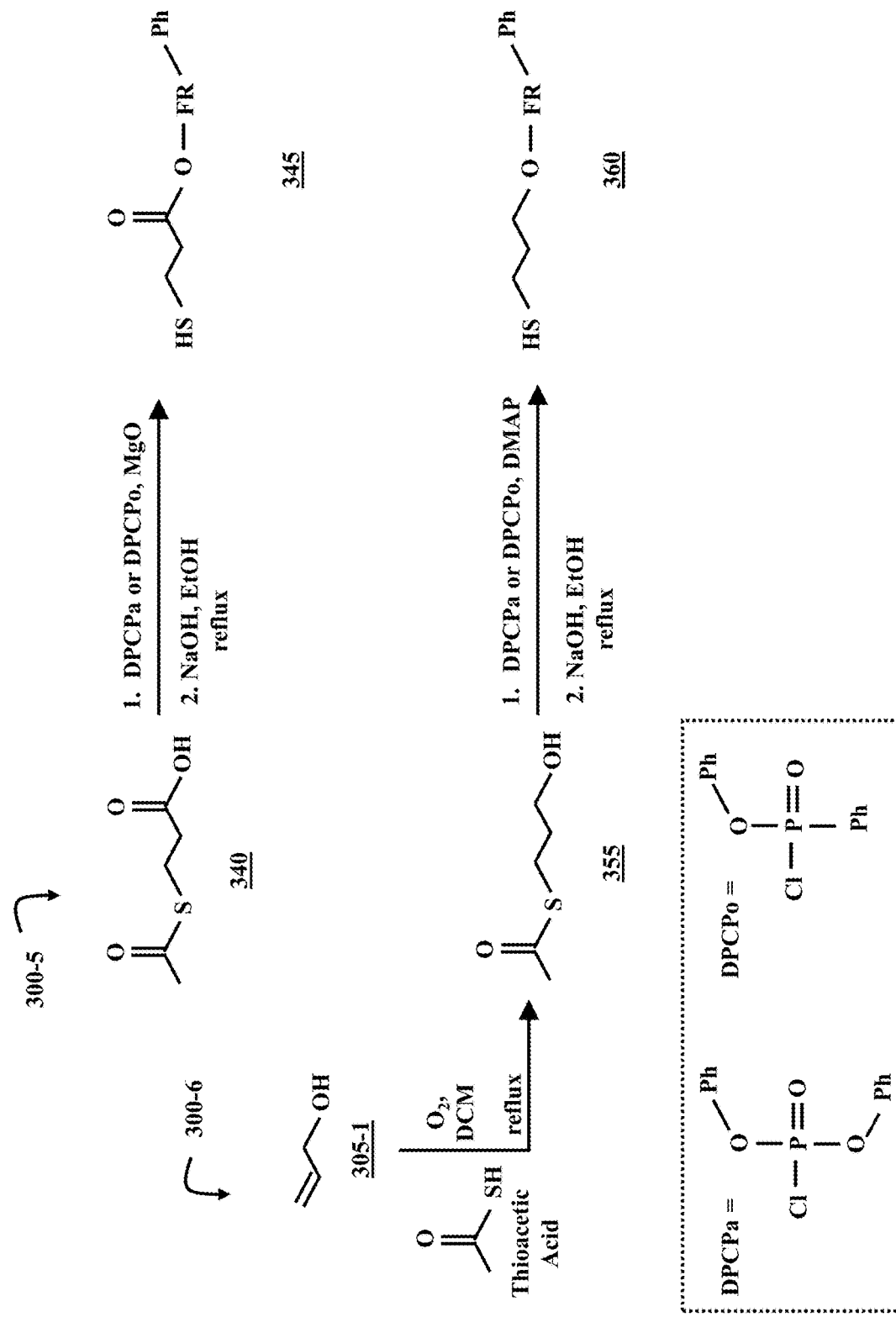
FIG. 3C is a chemical reaction diagram illustrating a process of synthesizing a carboxylic acid-derived flame-retardant thiol molecule and a process of synthesizing a hydroxy-derived flame-retardant thiol molecule, in accordance with embodiments of the present disclosure.

FIG. 3C is a chemical reaction diagram illustrating a process 300-5 of synthesizing a carboxylic acid-derived flame-retardant thiol molecule 345 and a process 300-6 of synthesizing a hydroxy-derived flame-retardant thiol molecule 360, in accordance with embodiments of the present disclosure. In process 300-5, acetate-protected thiopropionic acid 340 is reacted with magnesium oxide (MgO) and diphenyl chlorophosphate (DPCPa) or diphenylphosphinic chloride (DPCPo). The acetate group is then removed by refluxing the mixture in an ethanol (EtOH) solution containing sodium hydroxide (NaOH), yielding the carboxylic acid-derived flame-retardant thiol molecule 345. If the process is carried out with DPCPa, the carboxylic acid-derived flame-retardant thiol molecule 345 will have phosphoryl FR groups, and, if the reaction is carried out with DPCPo, the carboxylic acid-derived flame-retardant thiol molecule 345 will have phosphonyl FR groups.

In process 300-6, allyl alcohol 305-1 is reacted with thioacetic acid in a thiol-ene reaction. In the first step of the reaction, oxygen ($O_2$) is added to a dichloromethane (DCM) solution of the allyl alcohol 305-1 and thioacetic acid. The mixture is refluxed, resulting in an acetate-protected mercaptopropanol 355. The second step in the reaction is a substitution reaction involving diphenyl chlorophosphate (DPCPa) and catalytic dimethylaminopyridine (DMAP) or diphenylphosphinic chloride (DPCPo). The acetate group is removed by refluxing the mixture in an ethanol (EtOH) solution containing sodium hydroxide (NaOH). This step results in the production of the hydroxy-derived flame-retardant thiol molecule 360. If the process is carried out with DPCPa, the hydroxy-derived flame-retardant thiol molecule 360 will have phosphoryl FR groups, and, if the reaction is carried out with DPCPo, the hydroxy-derived flame-retardant thiol molecule 360 will have phosphonyl FR groups.

Figure 3D:
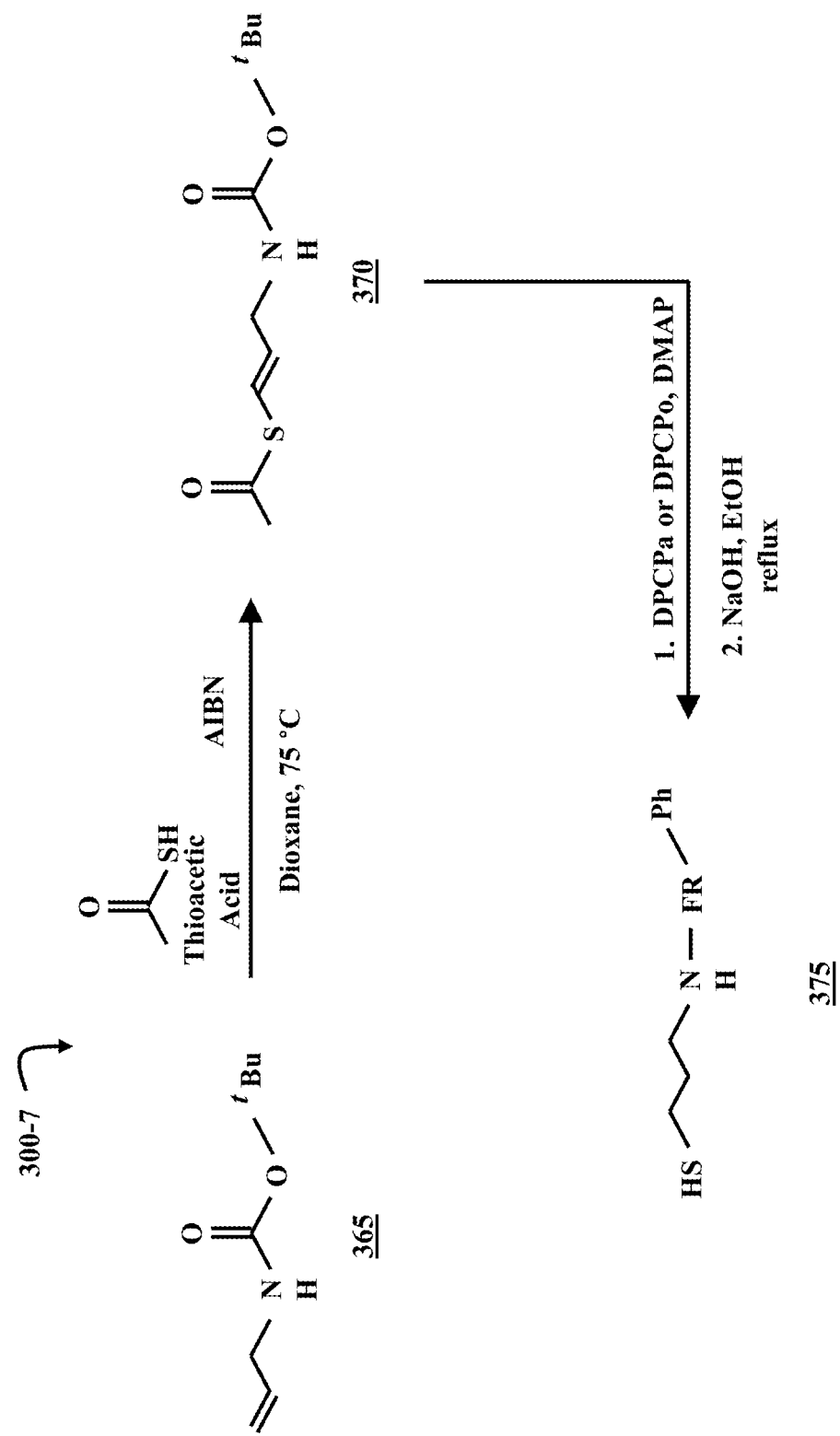
FIG. 3D is a chemical reaction diagram illustrating a process of synthesizing an amino-derived flame-retardant thiol molecule, in accordance with embodiments of the present disclosure.

FIG. 3D is a chemical reaction diagram illustrating a process 300-7 of synthesizing an amino-derived flame-retardant thiol molecule 375, in accordance with embodiments of the present disclosure. In process 300-7, 1-(boc-amino)-3-butene 365 is first reacted with thioacetic acid in a thiol-ene reaction. Azobisisobutyronitrile (AIBN) is added to the dioxane solution of 1-(boc-amino)-3-butene 365 and thioacetic acid, and the mixture is stirred at 75° C., resulting in an acetate-protected precursor 370 to the amino-derived flame-retardant thiol molecule 375. The second step in process 300-7 is a substitution reaction with diphenyl chlorophosphate (DPCPa) or diphenylphosphinic chloride (DPCPo) and catalytic dimethylaminopyridine (DMAP). The acetate group and boc groups are removed under basic conditions (e.g., by refluxing the mixture in an ethanol (EtOH) solution containing sodium hydroxide (NaOH)). This step results in the production of the amino-derived flame-retardant thiol molecule 375. If the process is carried out with DPCPa, the amino-derived flame-retardant thiol molecule 375 will have phosphoryl FR groups, and, if the reaction is carried out with DPCPo, the amino-derived flame-retardant thiol molecule 375 will have phosphonyl FR groups.

Figure 4:
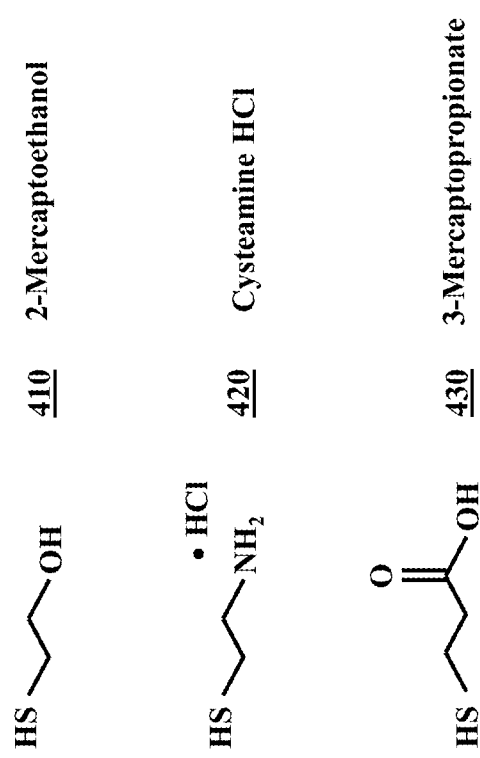
FIG. 4 is a diagrammatic representation of the molecular structures of three thiol molecules that are involved in the synthesis of the flame-retardant sorbitol-derived, glucaric acid-derived, or gluconic acid-derived molecules, in accordance with embodiments of the present disclosure.

FIG. 4 is a diagrammatic representation of the molecular structures of three thiol molecules that are involved in the synthesis of some examples of the flame-retardant sorbitol-derived, glucaric acid-derived, or gluconic acid-derived molecules, in accordance with embodiments of the present disclosure. The three thiol molecules are 2-mercaptoethanol 410, cysteamine hydrochloride (HCl) 420, and 3-mercaptopropionate 430. Each of these thiols can be involved in the synthesis of a thioether-linked flame-retardant derivative. In these syntheses, the thiol molecules provide thioether R groups. Details of the syntheses and structures of the thioether-linked flame-retardant sorbitol, glucaric acid, or gluconic acid derivatives are discussed in greater detail with regard to FIGS. 7A-7D.

Figure 5A:
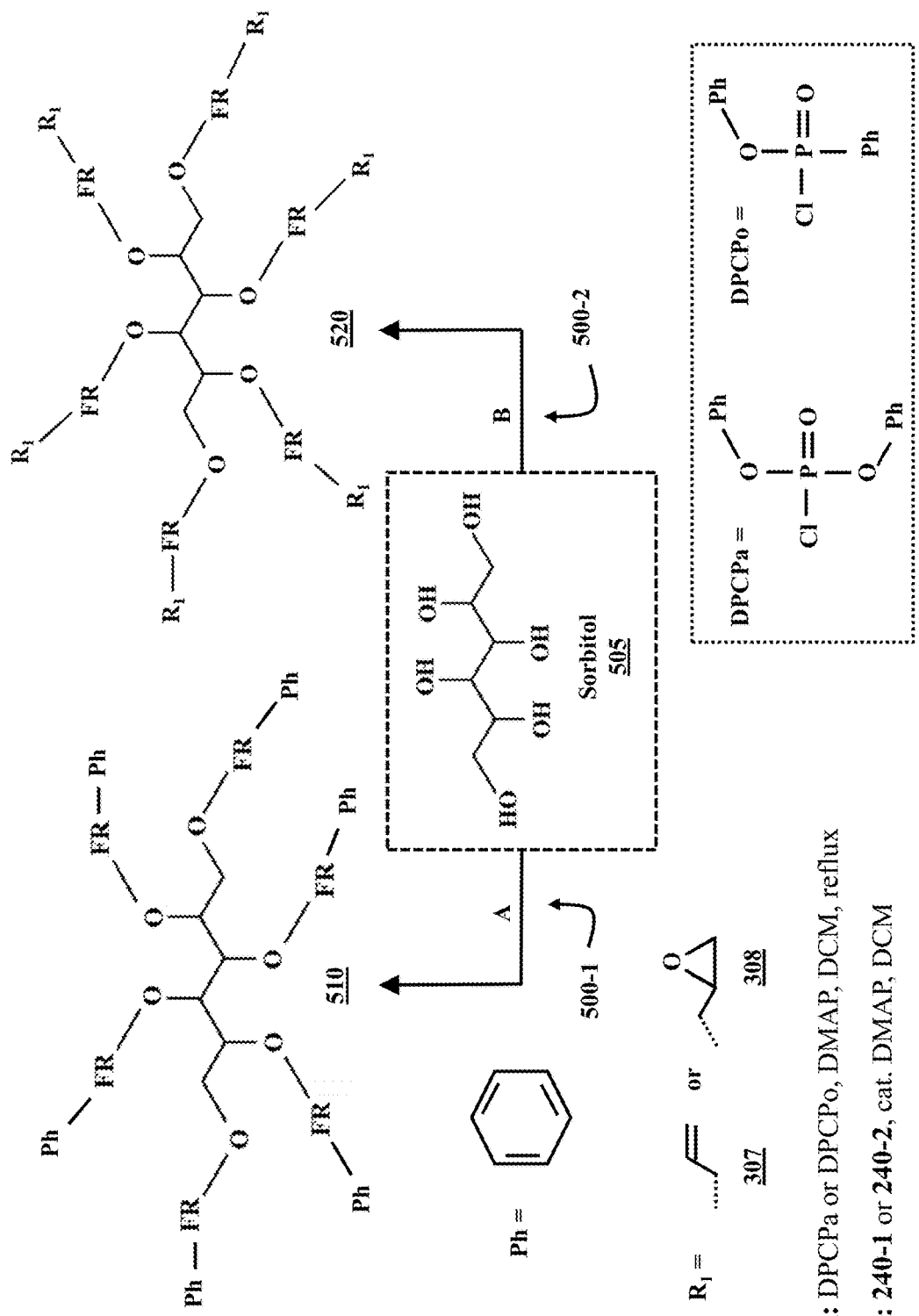
FIG. 5A is a chemical reaction diagram illustrating a process of synthesizing a flame-retardant sorbitol-derived small molecule and a process of forming an allyl-functionalized or an epoxy-functionalized flame-retardant sorbitol cross-linker, in accordance with embodiments of the present disclosure.

FIG. 5A is a chemical reaction diagram illustrating a process 500-1 of synthesizing a flame-retardant sorbitol-derived small molecule 510 and a process 500-2 of forming an allyl-functionalized or an epoxy-functionalized flame-retardant sorbitol cross-linker 520, in accordance with embodiments of the present disclosure. In process 500-1, sorbitol 505 is reacted with either diphenyl chlorophosphate (DPCPa) or diphenylphosphinic chloride (DPCPo). The mixture is refluxed with catalytic dimethylaminopyridine (DMAP) in a dichloromethane (DCM) solution, producing the flame-retardant sorbitol-derived small molecule 510. If the process is carried out with DPCPa, the flame-retardant sorbitol-derived small molecule 510 will have phosphoryl FR groups, and, if the reaction is carried out with DPCPo, the flame-retardant sorbitol-derived small molecule 510 will have phosphonyl FR groups.

In process 500-2, the sorbitol 505 is reacted with a phosphorus-based flame-retardant molecule 240 and catalytic dimethylaminopyridine (DMAP) in a dichloromethane (DCM) solution to yield the allyl-functionalized or the epoxy-functionalized flame-retardant sorbitol cross-linker 520. If sorbitol 505 is reacted with a phosphorus-based flame-retardant molecule 240 having an allyl $R_1$ group 307, the functionalized flame-retardant will be an allyl-functionalized flame-retardant sorbitol cross-linker (e.g., $R_1$ as shown on FIG. 5A will be an allyl functional group 307, see FIG. 5B). If sorbitol 505 is reacted with a phosphorus-based flame-retardant molecule 240 having an epoxy $R_1$ group 308, the functionalized flame-retardant will be an epoxy-functionalized flame-retardant sorbitol cross-linker (e.g., $R_1$ as shown on FIG. 5A will be an epoxy functional group 308, see FIG. 5B). If the reaction is carried out with phosphate-based flame-retardant molecule 240-1, the allyl-functionalized or epoxy-functionalized flame-retardant sorbitol cross-linker 520 will have a phosphoryl FR group, and, if the reaction is carried out with the phosphonate-based flame-retardant molecule 240-2, the allyl-functionalized or epoxy-functionalized flame-retardant sorbitol cross-linker 520 will have a phosphonyl FR group.

Figure 5B:
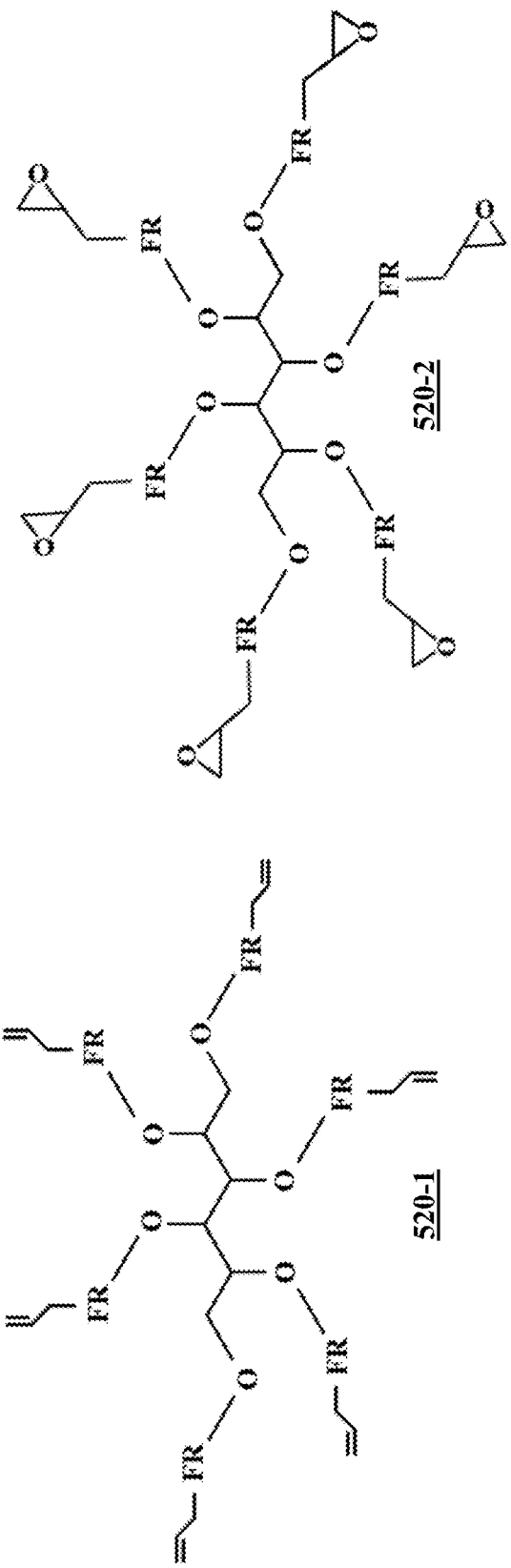
FIG. 5B is a chemical diagram illustrating an allyl-functionalized flame-retardant sorbitol cross-linker and an epoxy-functionalized flame-retardant sorbitol cross-linker, in accordance with embodiments of the present disclosure.

FIG. 5B is a chemical diagram illustrating an allyl-functionalized flame-retardant sorbitol cross-linker 520-1 and an epoxy-functionalized flame-retardant sorbitol cross-linker 520-2, in accordance with embodiments of the present disclosure. As mentioned with regard to FIG. 5A, if sorbitol 505 is reacted with a phosphorus-based flame-retardant molecule 240 having an allyl $R_1$ group 307, the functionalized flame-retardant will be the allyl-functionalized flame-retardant sorbitol cross-linker 520-1. If sorbitol 505 is reacted with a phosphorus-based flame-retardant molecule 240 having an epoxy $R_1$ group 308, the functionalized flame-retardant will be the epoxy-functionalized flame-retardant sorbitol cross-linker 520-2.

Figure 5C:
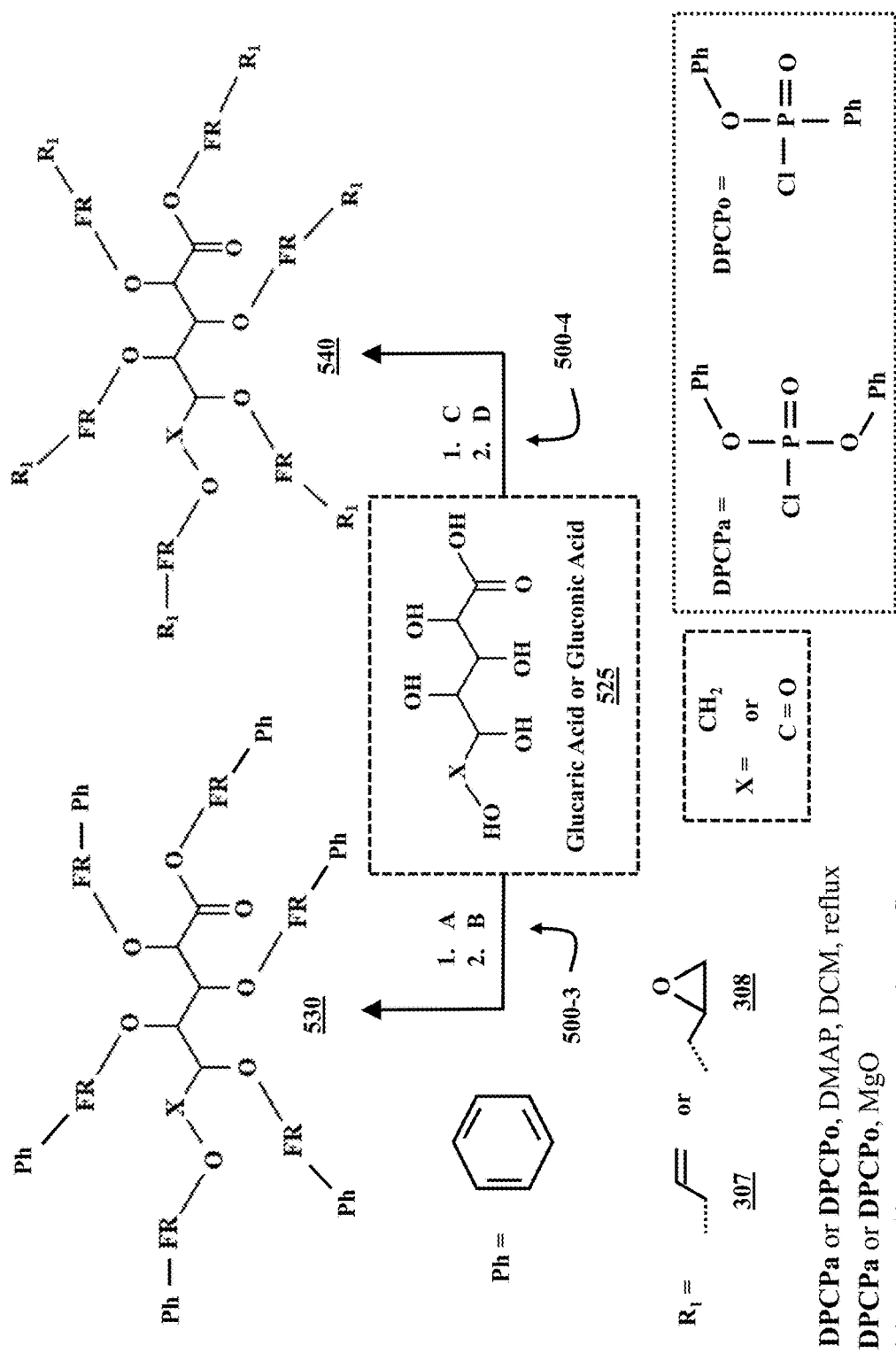
FIG. 5C is a chemical reaction diagram illustrating a process of synthesizing a flame-retardant glucaric acid-derived or gluconic acid-derived small molecule and a process of forming an allyl-functionalized or an epoxy-functionalized flame-retardant glucaric acid or gluconic acid cross-linker, in accordance with embodiments of the present disclosure.

FIG. 5C is a chemical reaction diagram illustrating a process 500-3 of synthesizing a flame-retardant glucaric acid-derived or gluconic acid-derived small molecule 530 and a process 500-4 of forming an allyl-functionalized or an epoxy-functionalized flame-retardant glucaric acid or gluconic acid cross-linker 540, in accordance with embodiments of the present disclosure. In process 500-3, the glucaric acid or gluconic acid 525 is reacted with either diphenyl chlorophosphate (DPCPa) or diphenylphosphinic chloride (DPCPo). The mixture is refluxed with catalytic dimethylaminopyridine (DMAP) in a dichloromethane (DCM) solution, producing the flame-retardant glucaric acid-derived or gluconic acid-derived small molecule 530. The precursor selected for reaction (e.g., gluconic acid or glucaric acid) determines whether the flame-retardant small molecule is glucaric acid-derived or gluconic acid-derived. For example, if X=$CH_2$ (methanediyl moiety), then a flame-retardant gluconic acid-derived small molecule 530 will be formed. If X=C=O (carbonyl moiety), then a flame-retardant glucaric acid-derived small molecule 530 will be formed. If the process is carried out with DPCPa, the flame-retardant glucaric acid-derived or gluconic acid-derived small molecule 530 will have phosphoryl FR groups, and, if the reaction is carried out with DPCPo, the flame-retardant glucaric acid-derived or gluconic acid-derived small molecule 530 will have phosphonyl FR groups.

In process 500-4, the glucaric acid or gluconic acid 525 is reacted with a phosphorus-based flame-retardant molecule 240 and catalytic dimethylaminopyridine (DMAP) in a dichloromethane (DCM) solution. The reaction between the glucaric acid or gluconic acid 525 and the phosphorus-based flame-retardant molecule 240 produces the allyl-functionalized or the epoxy-functionalized flame-retardant glucaric acid or gluconic acid cross-linker 540. The precursor selected (e.g., gluconic acid or glucaric acid) determines whether the flame-retardant is glucaric acid-derived or gluconic acid. For example, if X=$CH_2$ (methanediyl moiety), then a flame-retardant gluconic acid cross-linker will be formed. If X=C=O (carbonyl moiety), then a flame-retardant glucaric acid cross-linker will be formed. If glucaric acid or gluconic acid 525 is reacted with a phosphorus-based flame-retardant molecule 240 having an allyl $R_1$ group 307, the functionalized flame-retardant will be an allyl-functionalized flame-retardant gluconic acid or glucaric acid cross-linker (e.g., $R_1$ as shown on FIG. 5C will be an allyl functional group 307). If glucaric acid or gluconic acid 525 is reacted with a phosphorus-based flame-retardant molecule 240 having an epoxy R1 group 308, the functionalized flame-retardant will be an epoxy-functionalized flame-retardant gluconic acid or glucaric acid cross-linker (e.g., $R_1$ as shown on FIG. 5C will be an epoxy functional group 308). If the reaction is carried out with phosphate-based flame-retardant molecule 240-1, the allyl-substituted flame-retardant glucaric acid or gluconic acid cross-linker 540 will have a phosphoryl FR group, and, if the reaction is carried out with the phosphonate-based flame-retardant molecule 240-2, the allyl-substituted flame-retardant glucaric acid or gluconic acid-cross-linker 540 will have a phosphonyl FR group.

Figure 5D:
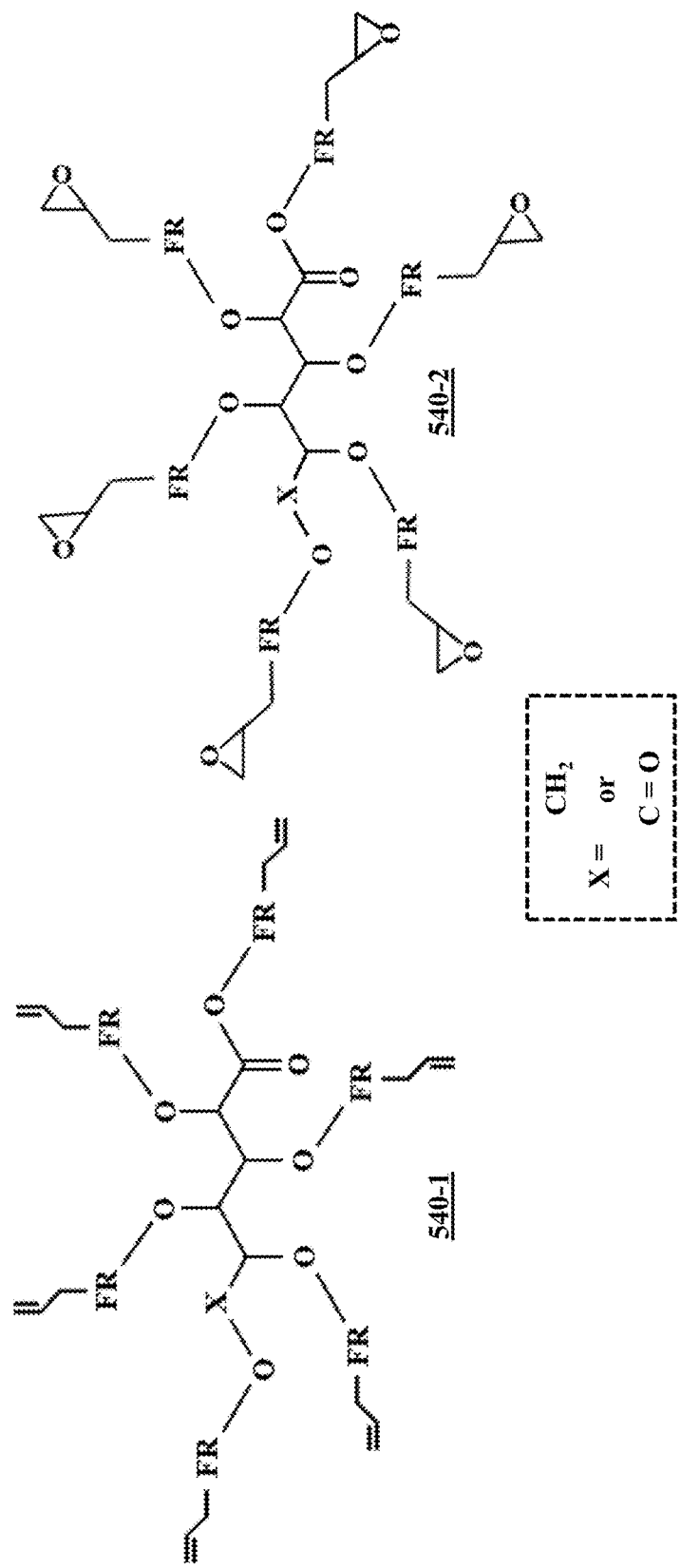
FIG. 5D is a chemical diagram illustrating an allyl-functionalized flame-retardant gluconic acid or glucaric acid cross-linker and an epoxy-functionalized flame-retardant gluconic acid or glucaric acid cross-linker, in accordance with embodiments of the present disclosure.

FIG. 5D is a chemical diagram illustrating an allyl-functionalized flame-retardant gluconic acid or glucaric acid cross-linker 540-1 and an epoxy-functionalized flame-retardant gluconic acid or glucaric acid cross-linker 540-2, in accordance with embodiments of the present disclosure. As mentioned with regard to FIG. 5C, if glucaric acid or gluconic acid 525 is reacted with a phosphorus-based flame-retardant molecule 240 having an allyl $R_1$ group 307, the functionalized flame-retardant will be the allyl-functionalized flame-retardant glucaric acid or gluconic acid cross-linker 540-1. If glucaric acid or gluconic acid 525 is reacted with a phosphorus-based flame-retardant molecule 240 having an epoxy $R_1$ group 308, the functionalized flame-retardant will be the epoxy-functionalized flame-retardant glucaric acid or gluconic acid cross-linker 540-2.

Figure 5E:
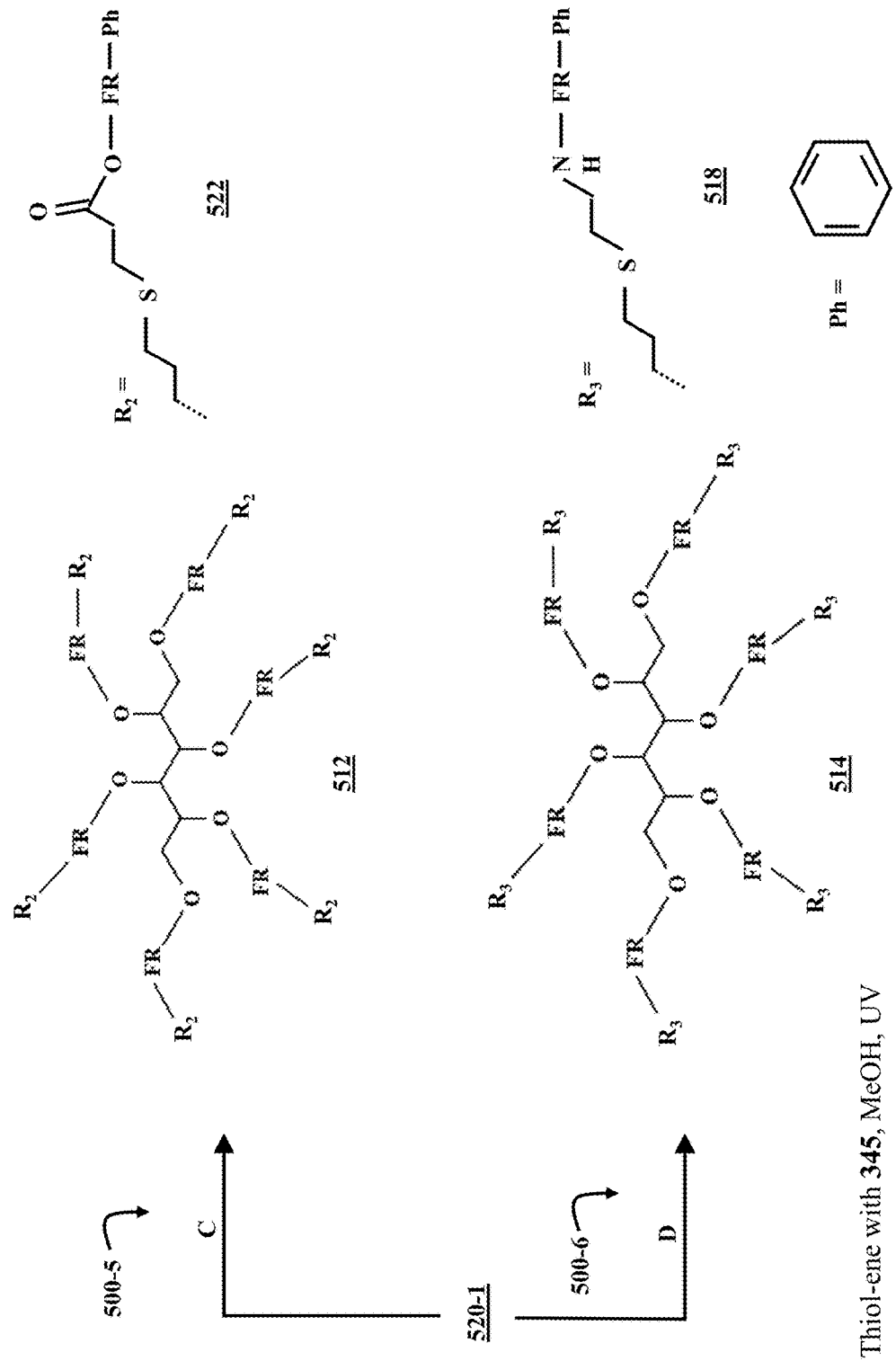
FIG. 5E and FIG. 5F are chemical reaction diagrams illustrating three processes of synthesizing thioether-linked flame-retardant sorbitol-derived small molecules, in accordance with embodiments of the present disclosure.
Figure 5F:
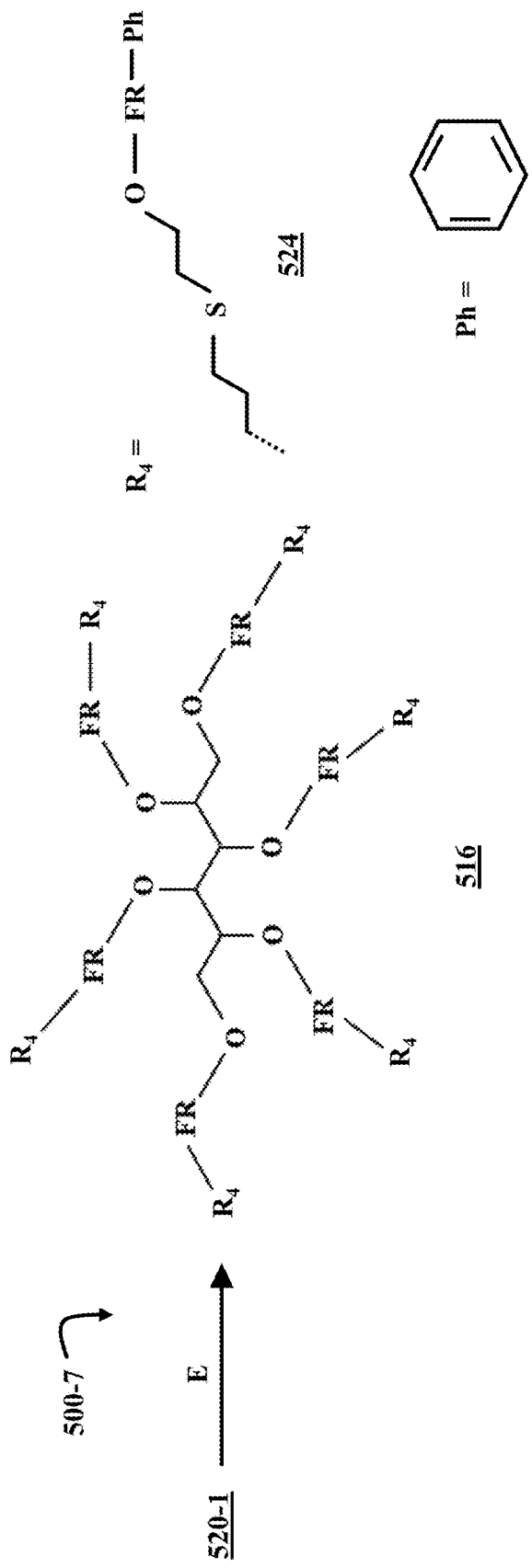

FIG. 5E and FIG. 5F are chemical reaction diagrams illustrating three processes 500-5, 500-6, 500-7 of synthesizing thioether-linked flame-retardant sorbitol-derived small molecules, in accordance with embodiments of the present disclosure. Each process is a thiol-ene reaction between the allyl-substituted flame-retardant sorbitol cross-linker 520-1 and a flame-retardant thiol molecule 345, 360, or 375. The syntheses and structures of the flame-retardant thiol molecules are discussed in greater detail with regard to FIGS. 3C and 3D.

In process 500-5, the allyl-functionalized flame-retardant sorbitol cross-linker 520-1 is reacted with the carboxylic acid-derived flame-retardant thiol molecule 345 under UV light in a methanol (MeOH) solution. The resulting thioether-linked flame-retardant sorbitol-derived small molecule 512 has a thioether $R_2$ group 522 that corresponds to the carboxylic acid-derived flame-retardant thiol molecule 345. In process 500-6, the allyl-functionalized flame-retardant sorbitol cross-linker 520-1 is reacted with the amino-derived flame-retardant thiol molecule 375 in a methanol (MeOH) solution with a pH of approximately 8-11 under UV light (e.g., light with a wavelength of approximately 100-410 nm). The resulting thioether-linked flame-retardant sorbitol-derived small molecule 514 has a thioether $R_3$ group 518 that corresponds to the amino-derived flame-retardant thiol molecule 375. In process 500-7, the allyl-functionalized flame-retardant sorbitol cross-linker 520-1 is reacted with the hydroxy-derived flame-retardant thiol molecule 360 under UV light. The resulting thioether-linked flame-retardant sorbitol-derived small molecule 516 has a thioether $R_4$ group 524 that corresponds to the hydroxy-derived flame-retardant thiol molecule 360.

Figure 5G:
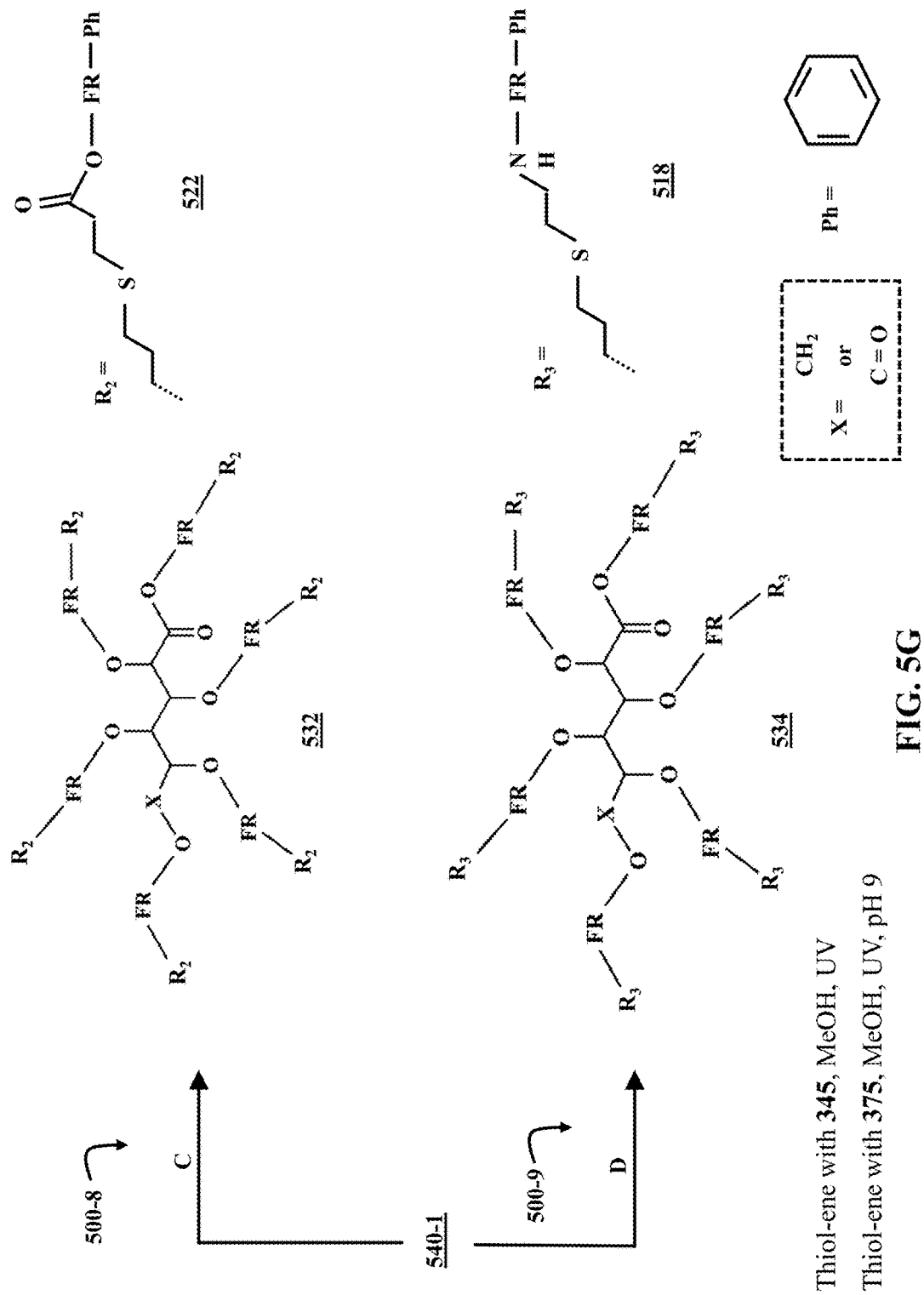
FIGS. 5G and 5H are chemical reaction diagrams illustrating three processes of synthesizing thioether-linked flame-retardant glucaric acid-derived or gluconic acid-derived small molecules, in accordance with embodiments of the present disclosure.
Figure 5H:
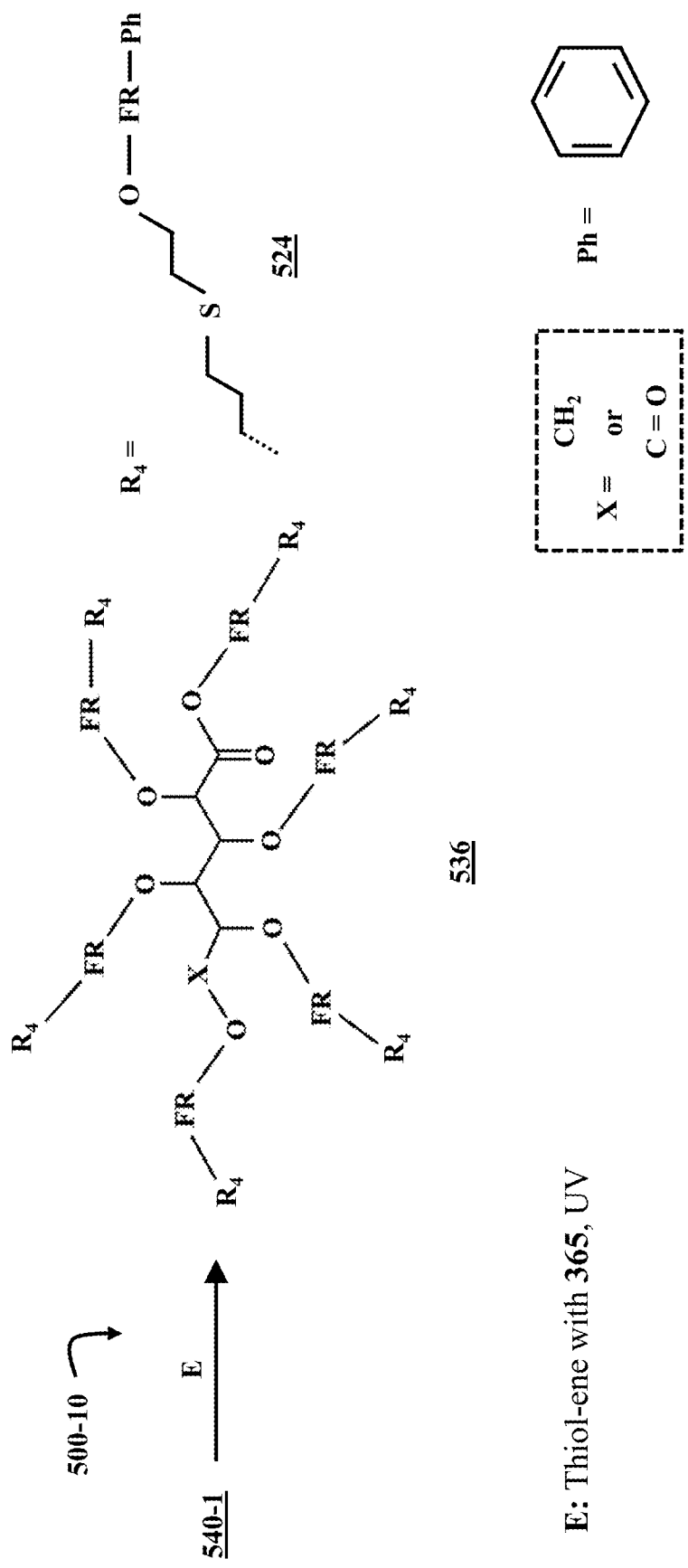

FIGS. 5G and 5H are chemical reaction diagrams illustrating three processes 500-8, 500-9, 500-10 of synthesizing thioether-linked flame-retardant glucaric acid-derived or gluconic acid-derived small molecules, in accordance with embodiments of the present disclosure. Each process is a thiol-ene reaction between the allyl-functionalized flame-retardant glucaric acid or gluconic acid cross-linker 540-1 and a flame-retardant thiol molecule 345, 360, or 375. The syntheses and structures of the flame-retardant thiol molecules are discussed in greater detail with regard to FIGS. 3C and 3D.

In process 500-8, the allyl-functionalized flame-retardant glucaric acid or gluconic acid cross-linker 540-1 is reacted with the carboxylic acid-derived flame-retardant thiol molecule 345 under UV light in a methanol (MeOH) solution. The resulting thioether-linked flame-retardant glucaric acid-derived or gluconic acid-derived small molecule 532 has the thioether $R_2$ group 522 that corresponds to the carboxylic acid-derived flame-retardant thiol molecule 345. In process 500-9, the allyl-functionalized flame-retardant glucaric acid or gluconic acid cross-linker 540-1 is reacted with the amino-derived flame-retardant thiol molecule 375 in a pH of approximately 8-11 methanol (MeOH) solution under UV light. The resulting thioether-linked flame-retardant glucaric acid-derived or gluconic acid-derived small molecule 534 has the thioether $R_3$ group 518 that corresponds to the amino-derived flame-retardant thiol molecule 375. In process 500-10, the allyl-functionalized flame-retardant glucaric acid or gluconic acid cross-linker 540-1 is reacted with the hydroxy-derived flame-retardant thiol molecule 360 under UV light. The resulting thioether-linked flame-retardant glucaric acid-derived or gluconic acid-derived small molecule 516 has the thioether $R_4$ group 524 that corresponds to the hydroxy-derived flame-retardant thiol molecule 360.

Figure 6A:
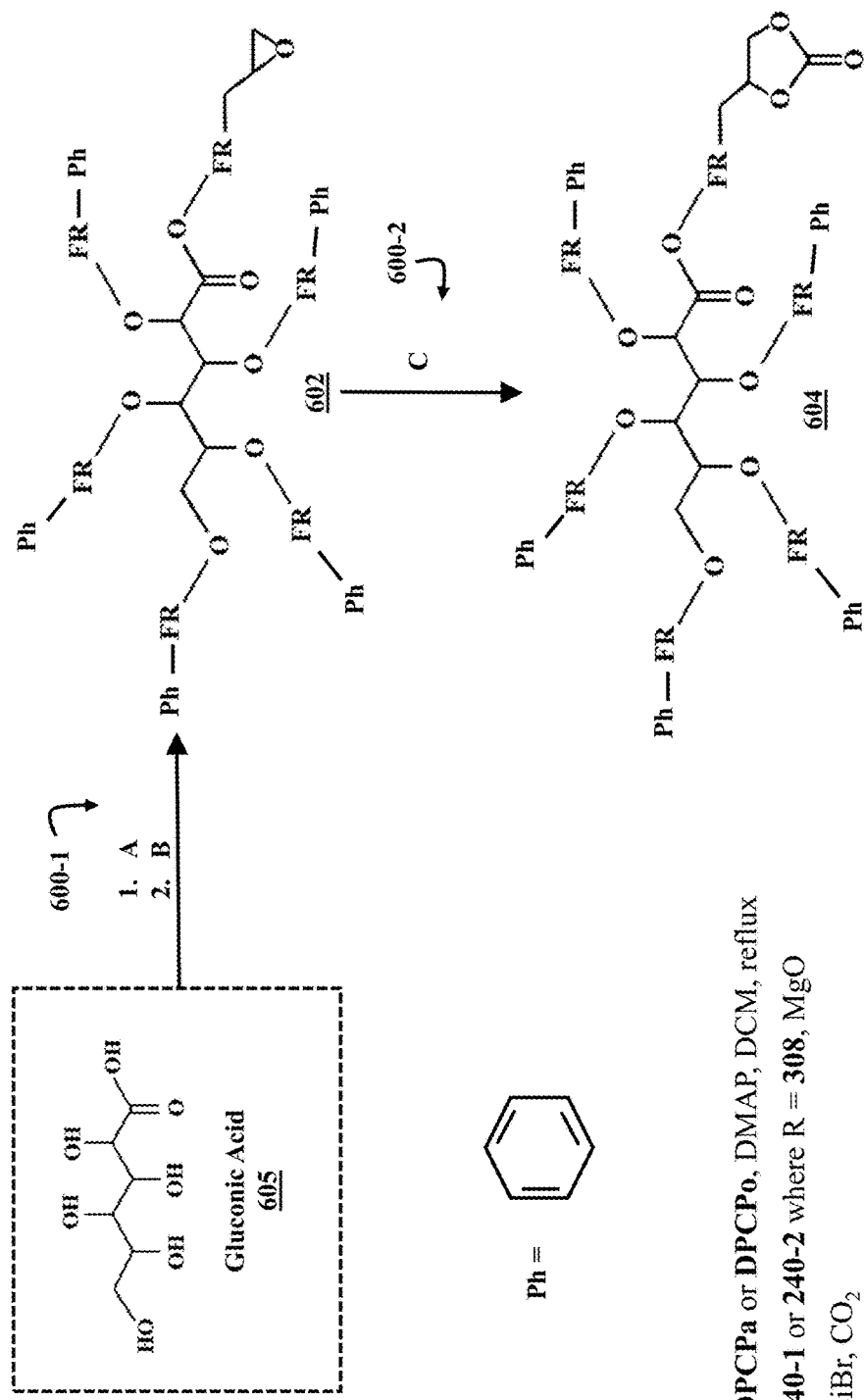
FIG. 6A is a chemical reaction diagram illustrating a process of synthesizing an epoxy monofunctionalized flame-retardant gluconic acid derivative and a process of synthesizing a propylene carbonate monofunctionalized flame-retardant gluconic acid derivative, in accordance with embodiments of the present disclosure.

FIG. 6A is a chemical reaction diagram illustrating a process 600-1 of synthesizing an epoxy monofunctionalized flame-retardant gluconic acid derivative 602 and a process 600-2 of synthesizing a propylene carbonate monofunctionalized flame-retardant gluconic acid derivative 604, in accordance with embodiments of the present disclosure. In process 600-1, gluconic acid 605 is reacted with either diphenyl chlorophosphate (DPCPa) or diphenylphosphinic chloride (DPCPo). The mixture is refluxed with catalytic dimethylaminopyridine (DMAP) in a dichloromethane (DCM) solution. In some embodiments, stoichiometric trimethylamine is used instead of DMAP. If the process is carried out with DPCPa, the epoxy monofunctionalized flame-retardant gluconic acid derivative 602 will have phosphoryl FR groups, and, if the reaction is carried out with DPCPo, the epoxy monofunctionalized flame-retardant gluconic acid derivative 602 will have phosphonyl FR groups. Further, in process 600-1, gluconic acid 605 is then reacted with the phosphorus-based flame-retardant molecule 240-1 or 240-2, where the $R_1$ functional group is an epoxy functional group 308, and magnesium oxide (MgO) to yield the epoxy functionalized flame-retardant gluconic acid derivative 602.

In process 600-2, the epoxy functionalized flame-retardant gluconic acid derivative 602 is combined with lithium bromide (LiBr). Carbon dioxide ($CO_2$) is added to the mixture, either by injecting it into the headspace of the reaction flask, or by bubbling it through the solution. This process yields the propylene carbonate functionalized flame-retardant gluconic acid derivative 604.

Figure 6B:
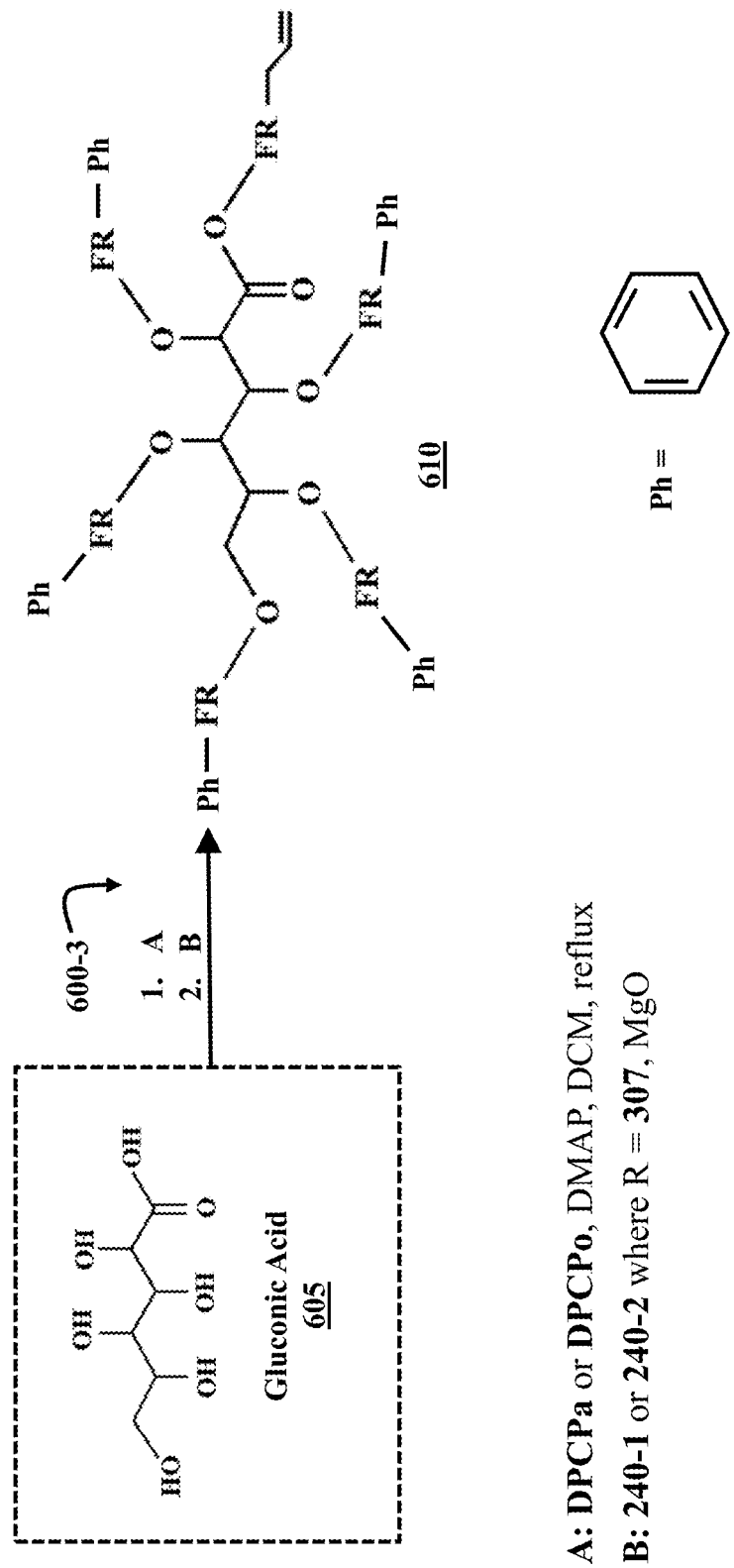
FIG. 6B is a chemical reaction diagram illustrating a process of synthesizing an allyl monofunctionalized flame-retardant gluconic acid derivative, in accordance with embodiments of the present disclosure.

FIG. 6B is a chemical reaction diagram illustrating a process 600-3 of synthesizing an allyl monofunctionalized flame-retardant gluconic acid derivative 610, in accordance with embodiments of the present disclosure. In process 600-3, gluconic acid 605 reacted with either diphenyl chlorophosphate (DPCPa) or diphenylphosphinic chloride (DPCPo). The mixture is refluxed with catalytic dimethylaminopyridine (DMAP) in a dichloromethane (DCM) solution. In some embodiments, stoichiometric trimethylamine is used instead of DMAP. If the process is carried out with DPCPa, the allyl monofunctionalized flame-retardant gluconic acid derivative 610 will have phosphoryl FR groups, and, if the reaction is carried out with DPCPo, the allyl monofunctionalized flame-retardant gluconic acid derivative 610 will have phosphonyl FR groups. Further, in process 600-3, gluconic acid 605 is then reacted with the phosphorus flame-retardant molecule 240-1 or 240-2, where the $R_1$ functional group is an allyl functional group 307, and magnesium oxide (MgO) to yield the allyl monofunctionalized flame-retardant gluconic acid-derived molecule 610.

Figure 6C:
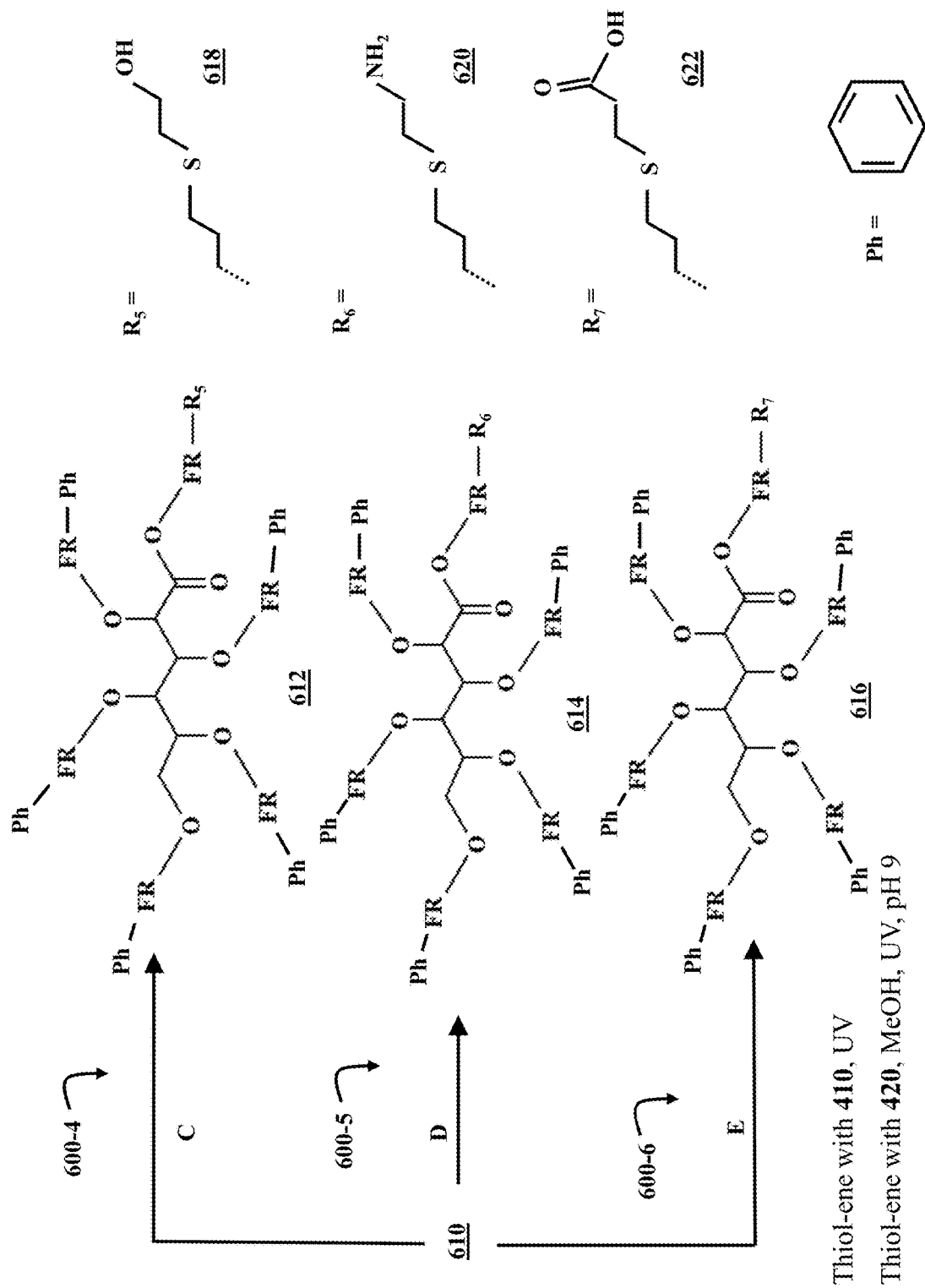
FIG. 6C is a chemical reaction diagram illustrating three processes of synthesizing monofunctionalized thioether-linked flame-retardant gluconic acid derivatives, in accordance with embodiments of the present disclosure.

FIG. 6C is a chemical reaction diagram illustrating three processes 600-4, 600-5, and 600-6 of synthesizing monofunctionalized thioether-linked flame-retardant gluconic acid derivatives, in accordance with embodiments of the present disclosure. Each process is a thiol-ene reaction between the allyl monofunctionalized flame-retardant gluconic acid derivative 610 and a thiol molecule. The thiol molecules used in processes 600-4, 600-5, and 600-6 are 2-mercaptoethanol 410, cysteamine HCl 420, and 3-mercaptopropionate 430, respectively. The structures of these thiol molecules are illustrated in FIG. 4.

In process 600-4, the allyl monofunctionalized flame-retardant gluconic acid derivative 610 is reacted with 2-mercaptoethanol 410 under UV light. The resulting hydroxyl monofunctionalized flame-retardant gluconic derivative 612 has a thioether $R_5$ group 618 that corresponds to 2-mercaptoethanol 410. In process 600-5, the allyl monofunctionalized flame-retardant gluconic acid derivative 610 is reacted with cysteamine HCl 420 in a pH of approximately 8-11 methanol (MeOH) solution under UV light. The resulting amino monofunctionalized flame-retardant gluconic acid derivative 614 has a thioether $R_6$ group 620 that corresponds to cysteamine HCl 420. In process 600-6, the allyl monofunctionalized flame-retardant gluconic acid derivative 610 is reacted with 3-mercaptopropionate 430 under UV light in a methanol (MeOH) solution. The resulting carboxylic-acid monofunctionalized flame-retardant gluconic acid-derived molecule 616 has a thioether $R_7$ group 622 that corresponds to 3-mercaptopropionate 430.

With reference to FIG. 6A-C, reacting gluconic acid 605 with a flame-retardant molecule (e.g., DPCPa, DPCPo, 240-1, and 240-2) and refluxing with catalytic dimethylaminopyridine (DMAP) in a dichloromethane (DCM) solution targets the hydroxyl functional groups of the gluconic acid 605 molecule that are not part of the carboxylic acid functional group for flame-retardant binding. On the contrary, reacting gluconic acid 605 with a flame-retardant molecule and magnesium oxide (MgO) targets the carboxylic acid functional group of the gluconic acid 605 for flame-retardant binding. Accordingly, reacting gluconic acid 605 with diphenyl chlorophosphate (DPCPa) or diphenylphosphinic chloride (DPCPo) and refluxing with DMAP in a DCM solution targets the hydroxyl groups on the molecule for flame-retardant binding, yielding five diphenyl flame-retardant groups on the gluconic acid 605 molecule (e.g., due to the five hydroxyl functional groups on gluconic acid). Afterwards, if the resulting gluconic acid molecule with five bound diphenyl flame-retardant groups is reacted with a functionalized flame-retardant molecule (e.g., 240-1 or 240-2, where $R_1$=308) in the presence of magnesium oxide (MgO), then the carboxylic acid functional group reacts with the functionalized flame-retardant, and yields a monofunctionalized molecule.

A similar reaction may be implemented to yield a pentafunctionalized gluconic acid molecule. For example, to yield an epoxy pentafunctionalized flame-retardant gluconic acid derivative, gluconic acid 605 may first be reacted with 240-1 or 240-2, where the functional $R_1$ group is an epoxy group 308. The mixture may then be refluxed with DMAP in a DCM solution to bind the epoxy-functionalized flame retardant molecules onto the hydroxyl functional groups. Afterwards, the resulting gluconic acid derivative (e.g., with five bound epoxy functionalized flame-retardant molecules) may be reacted with DPCPa or DPCPo and magnesium oxide (MgO) to yield the epoxy pentafunctionalized flame-retardant gluconic acid derivative. Similarly, to yield an allyl pentafunctionalized flame-retardant gluconic acid derivative, gluconic acid 605 may first be reacted with 240-1 or 240-2, where the functional $R_1$ group is an allyl group 307. The mixture may then be refluxed with DMAP in a DCM solution to bind the allyl-functionalized flame retardant molecules onto the hydroxyl functional groups. Afterwards, the resulting gluconic acid derivative (e.g., with five bound allyl functionalized flame-retardant molecules) may be reacted with DPCPa or DPCPo and magnesium oxide (MgO) to yield the allyl pentafunctionalized flame-retardant gluconic acid derivative.

The same reaction conditions as implemented in process 600-2 may be implemented to convert the epoxy pentafunctionalized flame-retardant gluconic acid derivative into propylene carbonate pentafunctionalized flame-retardant gluconic acid derivative (e.g., LiBr, $CO_2$). The same reaction conditions as implemented in processes 600-4, 600-5, and 600-6 may be implemented to convert the allyl pentafunctionalized flame-retardant gluconic acid derivative into a hydroxyl-thioether pentafunctionalized flame-retardant (e.g., 2-mercaptoethanol 380 under UV light), an aminothioether pentafunctionalized flame-retardant gluconic acid derivative (e.g., cysteamine HCl 385 in a pH of approximately 8-11 MeOH solution), or a carboxylic-acid-thioether pentafunctionalized flame-retardant gluconic acid derivative (e.g., 3-mercaptopropionate 390 under UV light in a MeOH solution), respectively.

Figure 7A:
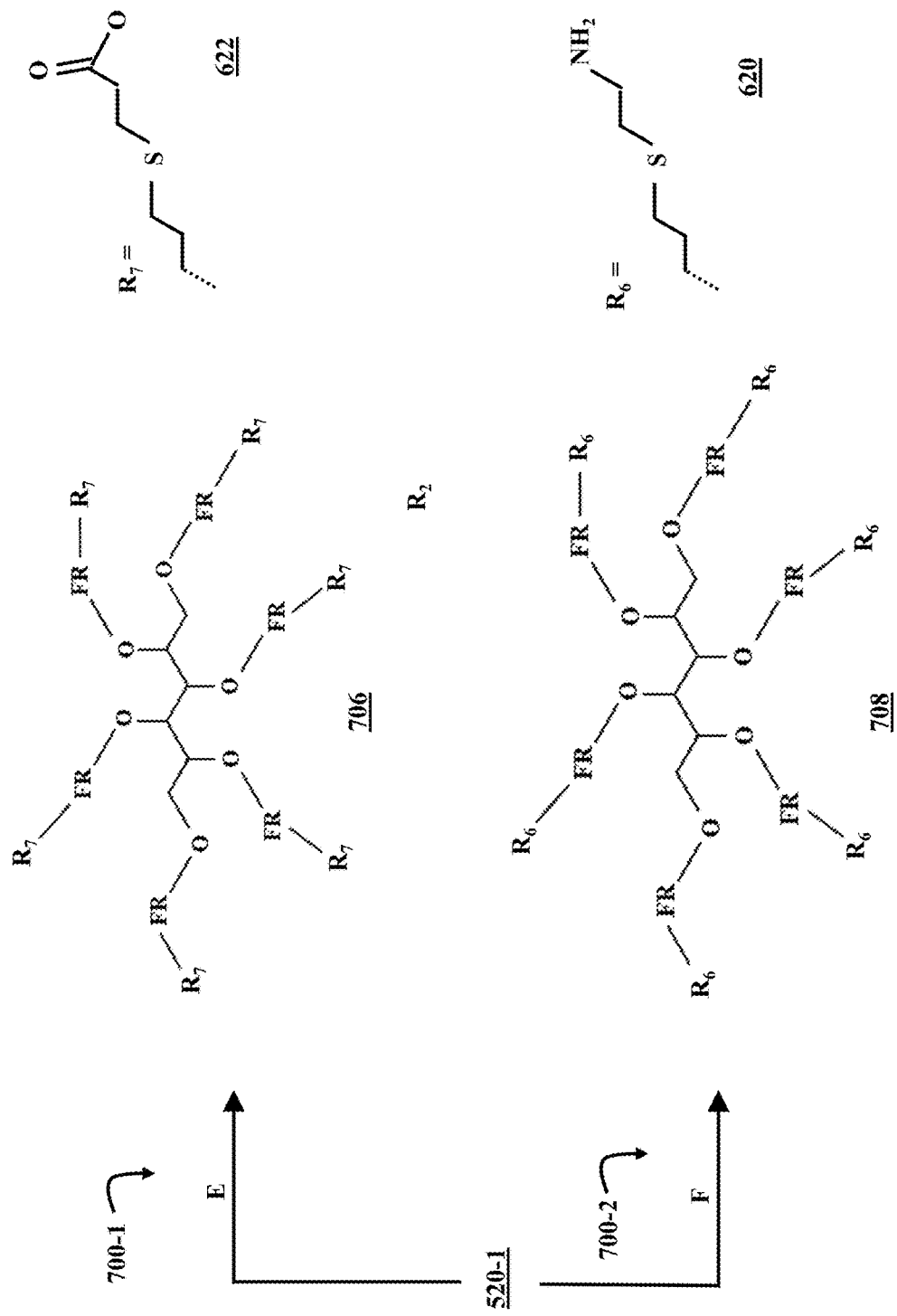
FIG. 7A and FIG. 7B are chemical reaction diagrams illustrating three processes of synthesizing thioether-linked flame-retardant sorbitol-derived cross-linkers, in accordance with embodiments of the present disclosure.
Figure 7B:
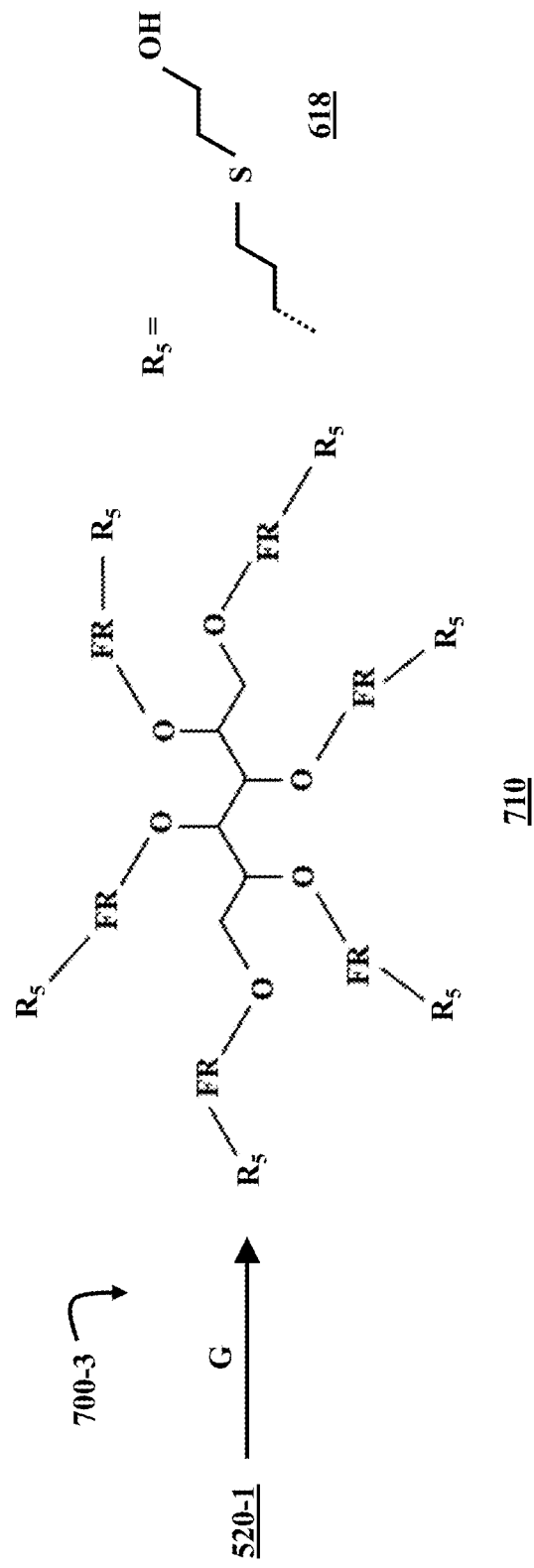

FIG. 7A and FIG. 7B are chemical reaction diagrams illustrating three processes 700-1, 700-2, and 700-3 of synthesizing thioether-linked flame-retardant sorbitol-derived cross-linkers, in accordance with embodiments of the present disclosure. Each process is a thiol-ene reaction between the allyl-functionalized flame-retardant sorbitol cross-linker 520-1 and a thiol molecule. The thiol molecules used in processes 700-1, 700-2, and 700-3 are 2-mercaptoethanol 410, cysteamine HCl 420, and 3-mercaptopropionate 430, respectively. The structures of these thiol molecules are illustrated in FIG. 4.

In process 700-1, the allyl-functionalized flame-retardant sorbitol cross-linker 520-1 is reacted with 2-mercaptopropionate 430 under UV light in a methanol (MeOH) solution. The resulting carboxylic acid-functionalized flame-retardant sorbitol-derived cross-linker 706 has thioether $R_7$ groups 622 that correspond to 3-mercaptopropionate 430. In process 700-2 the allyl-functionalized flame-retardant sorbitol cross-linker 520-1 is reacted with cysteamine HCl 420 in a pH of approximately 8-11 methanol (MeOH) solution under UV light. The resulting amino-functionalized flame-retardant sorbitol-derived cross-linker 708 has thioether $R_6$ groups 620 that correspond to cysteamine HCl 420. In process 700-3, as illustrated on FIG. 7B, the allyl-functionalized flame-retardant sorbitol cross-linker 520-1 is reacted with 2-mercaptoethanol 410 under UV light. The resulting hydroxyl-functionalized flame-retardant sorbitol-derived cross-linker 710 has thioether $R_5$ groups 618 that correspond to 2-mercaptoethanol 410.

Figure 7C:
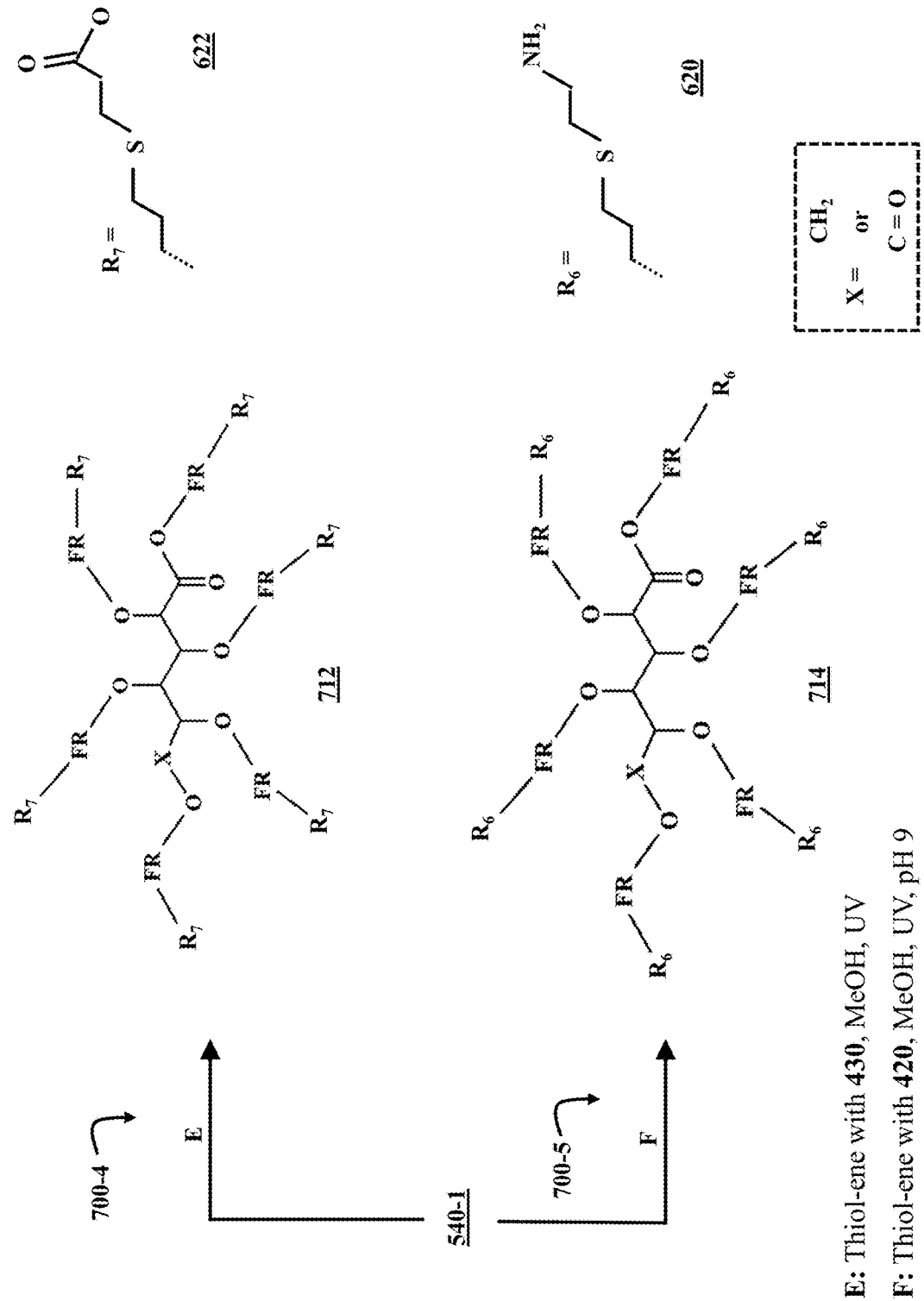
FIG. 7C and FIG. 7D are chemical reaction diagrams illustrating three processes of synthesizing thioether-linked flame-retardant gluconic acid-derived or glucaric acid-derived cross-linkers, in accordance with embodiments of the present disclosure.
Figure 7D:
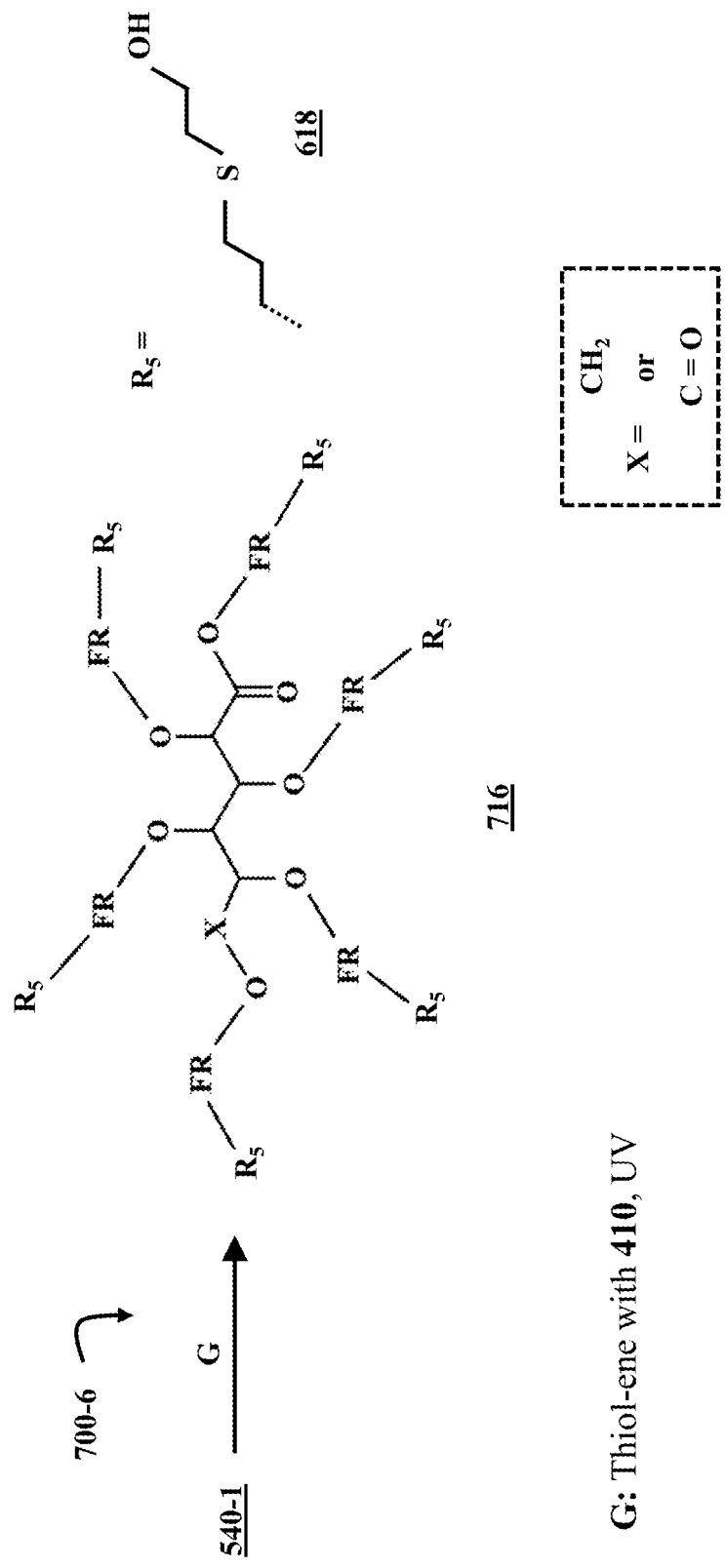

FIG. 7C and FIG. 7D are chemical reaction diagrams illustrating three processes 700-4, 700-5, and 700-6 of synthesizing thioether-linked flame-retardant gluconic acid-derived or glucaric acid-derived cross-linkers, in accordance with embodiments of the present disclosure. Each process is a thiol-ene reaction between the allyl-functionalized flame-retardant gluconic acid or glucaric acid cross-linker 540-1 and a thiol molecule. The thiol molecules used in processes 700-4, 700-5, and 700-6 are 2-mercaptoethanol 410, cysteamine HCl 420, and 3-mercaptopropionate 430, respectively. The structures of these thiol molecules are illustrated in FIG. 4.

In process 700-4 the allyl-functionalized flame-retardant gluconic acid or glucaric acid cross-linker 540-1 is reacted with 2-mercaptopropionate 430 under UV light in a methanol (MeOH) solution. The resulting carboxylic acid-functionalized flame-retardant gluconic acid-derived or glucaric acid-derived cross-linker 712 has thioether $R_7$ groups 622 that correspond to 3-mercaptopropionate 430. In process 700-5 the allyl-functionalized flame-retardant gluconic acid or glucaric acid cross-linker 540-1 is reacted with cysteamine HCl 420 in a pH of approximately 8-11 methanol (MeOH) solution under UV light. The resulting amino-functionalized flame-retardant gluconic acid-derived or glucaric acid-derived cross-linker 714 has thioether $R_6$ groups 620 that correspond to cysteamine HCl 420. In process 700-6, as illustrated on FIG. 7D, the allyl-functionalized flame-retardant gluconic acid or glucaric acid cross-linker 540-1 is reacted with 2-mercaptoethanol 410 under UV light. The resulting hydroxyl-functionalized flame-retardant gluconic acid-derived or glucaric acid-derived cross-linker 716 has thioether $R_5$ groups 618 that correspond to 2-mercaptoethanol 410.

Figure 7E:
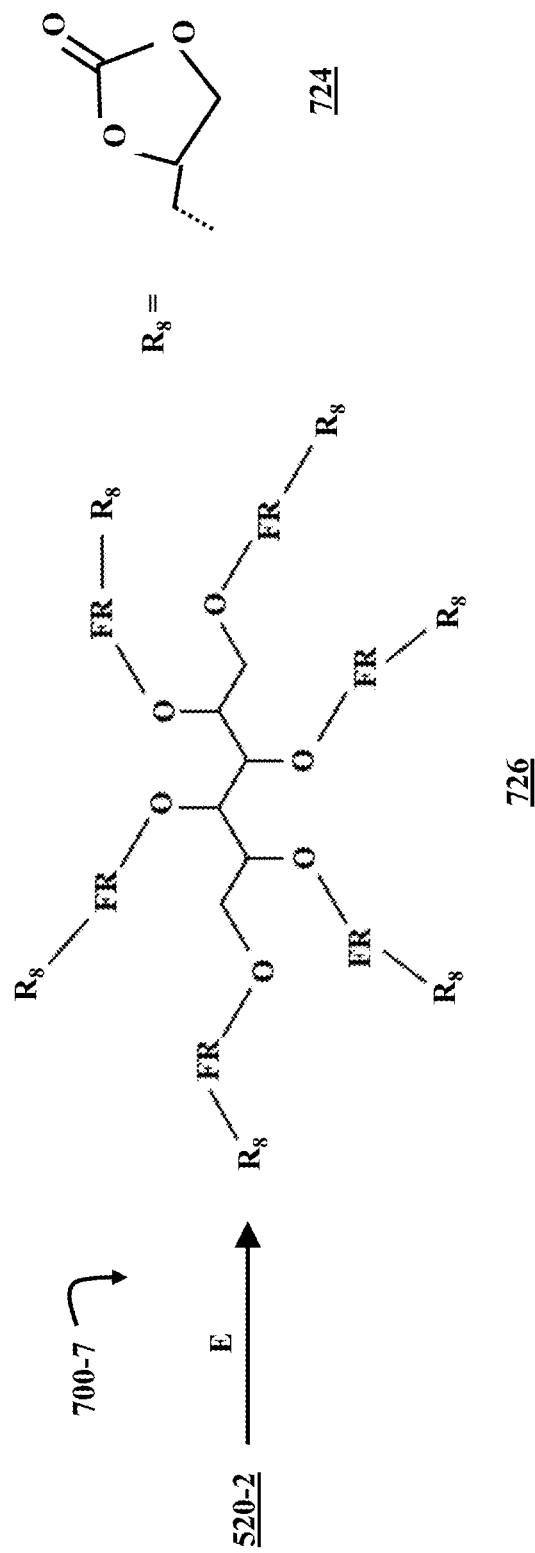
FIG. 7E is a chemical reaction diagram illustrating a process of synthesizing a propylene carbonate-functionalized flame-retardant sorbitol-derived cross-linker, in accordance with embodiments of the present disclosure.

FIG. 7E is a chemical reaction diagram illustrating a process 700-7 of synthesizing a propylene carbonate-functionalized flame-retardant sorbitol-derived cross-linker 726, in accordance with embodiments of the present disclosure. The epoxy-functionalized flame-retardant sorbitol cross-linker 520-2 is combined with lithium bromide (LiBr). Carbon dioxide ($CO_2$) is added to the mixture, either by injecting into the headspace of the reaction flask, or by bubbling through the solution. This step yields the propylene carbonate-functionalized flame-retardant sorbitol-derived cross-linker 726 with a propylene carbonate $R_8$ functional group 724.

Figure 7F:
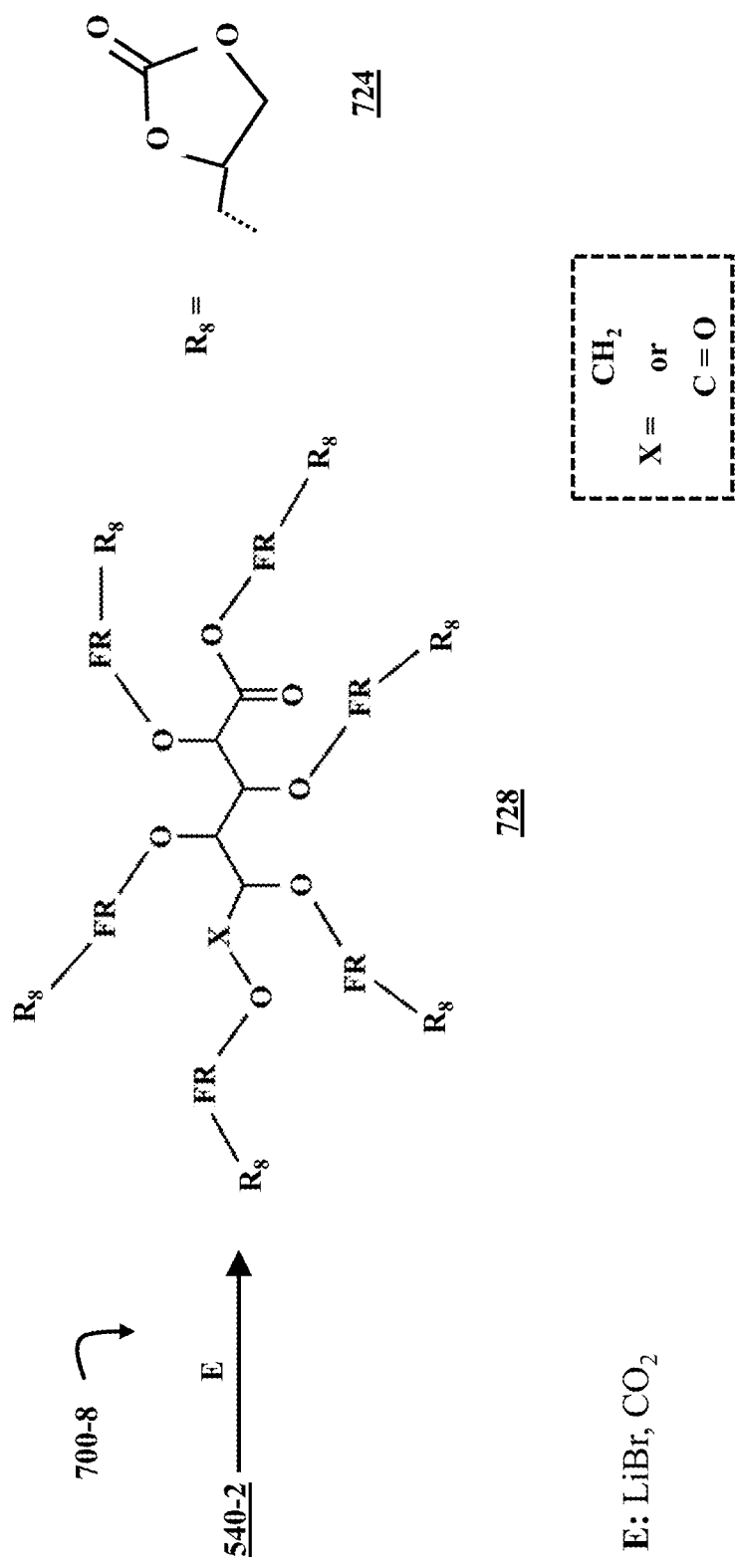
FIG. 7F is a chemical reaction diagram illustrating a process of synthesizing a propylene carbonate-functionalized flame-retardant gluconic acid-derived or glucaric acid-derived cross-linker, in accordance with embodiments of the present disclosure.

FIG. 7F is a chemical reaction diagram illustrating a process 700-8 of synthesizing a propylene carbonate-functionalized flame-retardant gluconic acid-derived or glucaric acid-derived cross-linker 728, in accordance with embodiments of the present disclosure. The epoxy-functionalized flame-retardant gluconic acid or glucaric acid cross-linker 540-2 is combined with lithium bromide (LiBr). Carbon dioxide ($CO_2$) is added to the mixture, either by injecting into the headspace of the reaction flask, or by bubbling through the solution. This step yields the propylene carbonate-functionalized flame-retardant gluconic acid-derived or glucaric acid-derived cross-linker 728 with a propylene carbonate $R_8$ functional group 724.

With respect to FIGS. 8A-8G, step A may refer to binding diphenyl flame-retardants (e.g., DPCPa/DPCPo) onto hydroxyl functional groups (e.g., via DMAP, DCM, reflux). Step B may refer to deprotecting protected polyols, monocarboxylic acids, and/or dicarboxylic acids. Step C may refer to binding functionalized flame-retardants (e.g., 240-1, 240-2, where $R_1$=307, 308) onto hydroxyl functional groups (e.g., via DMAP, DCM, reflux). Step D may refer to binding diphenyl flame-retardants (e.g., DPCPa/DPCPo) onto carboxylic acid functional groups (e.g., via MgO). Step E may refer to binding functionalized flame retardants (e.g., 240-1, 240-2, where $R_1$=307, 308) onto carboxylic acid functional groups (e.g., via MgO).

"L" in FIGS. 8A-8G represents a functional linker provided by an allyl-functionalized 307, epoxy-functionalized 308, or propylene carbonate-functionalized 724 group. The choice of reaction steps determines the identity of the R group. For example, step C (Functional Linker FR on Hydroxyls) may include reacting a precursor with 240-1 or 240-2 where $R_1$=307 and refluxing with catalytic dimethylaminopyridine (DMAP) in a dichloromethane (DCM) solution for allyl-functionalized derivatives. Alternatively, step C may include reacting a precursor with 240-1 or 240-2 where $R_1$=308 and refluxing with catalytic dimethylaminopyridine (DMAP) in a dichloromethane (DCM) solution for epoxy-functionalized derivatives. Step C may further include reacting the epoxy-functionalized derivatives with lithium bromide (LiBr) and carbon dioxide ($CO_2$) to yield propylene carbonate functionalized derivatives. It is noted that the allyl, epoxy, and propylene carbonate functionalized derivatives obtained in step C have functionalized linkers "L" bound to hydroxyl functional groups. Step D (Functional Linker FR on Carboxylic Acids) may include reacting a precursor with 240-1 or 240-2 where $R_1$=307 and magnesium oxide (MgO) for allyl-functionalized derivatives. Alternatively, step D may include reacting a precursor with 240-1 or 240-2 where $R_1$=308 and magnesium oxide (MgO) for epoxy-functionalized derivatives. Step D may further include reacting the epoxy-functionalized derivatives with lithium bromide (LiBr) and carbon dioxide ($CO_2$) to yield propylene carbonate functionalized derivatives. It is noted that the allyl, epoxy, and propylene carbonate functionalized derivatives obtained in step D have functionalized linkers "L" bound to carboxylic acid functional groups.

Step B (deprotection) may include removing a protecting group from a polyol (e.g., sorbitol), monoacid (e.g., gluconic acid), or diacid (e.g., glucaric acid). Deprotecting conditions may vary. Deprotection may include mixing protected polyols, monoacids, or diacids in acetone solutions, -p-toluenesulfonic acid (p-TsOH) solutions or hydrochloric acid (HCl) solutions. For example, a polyol, monoacid, or diacid may be deprotected at approximately pH 7 in the presence of acetone with indium(III) trifluoromethanesulfonate as a catalyst at room temperature. Deprotection may also be achieved by using a catalytic amount of sodium tetrakis (3,5-trifluoromethylphenyl) borate ($NaBArF_4$) (e.g., 0.1 molar % $NaBArF_4$) in water at 30° C. Alternatively, deprotection may be achieved by using a catalytic amount of erbium(III) trifluoromethanesulfonate) ($Er(OTf)_3$) (e.g., 1-5 molar % $Er(OTf)_3$) at room temperature in nitromethane. Deprotection may also be achieved by using a catalytic amount of cerium(III) triflate ($Ce(OTf)_3$) (5-30 molar % $Ce(OTf)_3$) at room temperature in nitromethane. Deprotection may be achieved at approximately pH 7 in the presence of a catalytic amount of iodine ($I_2$) in an acetone solution at 25° C.

Figure 8A:
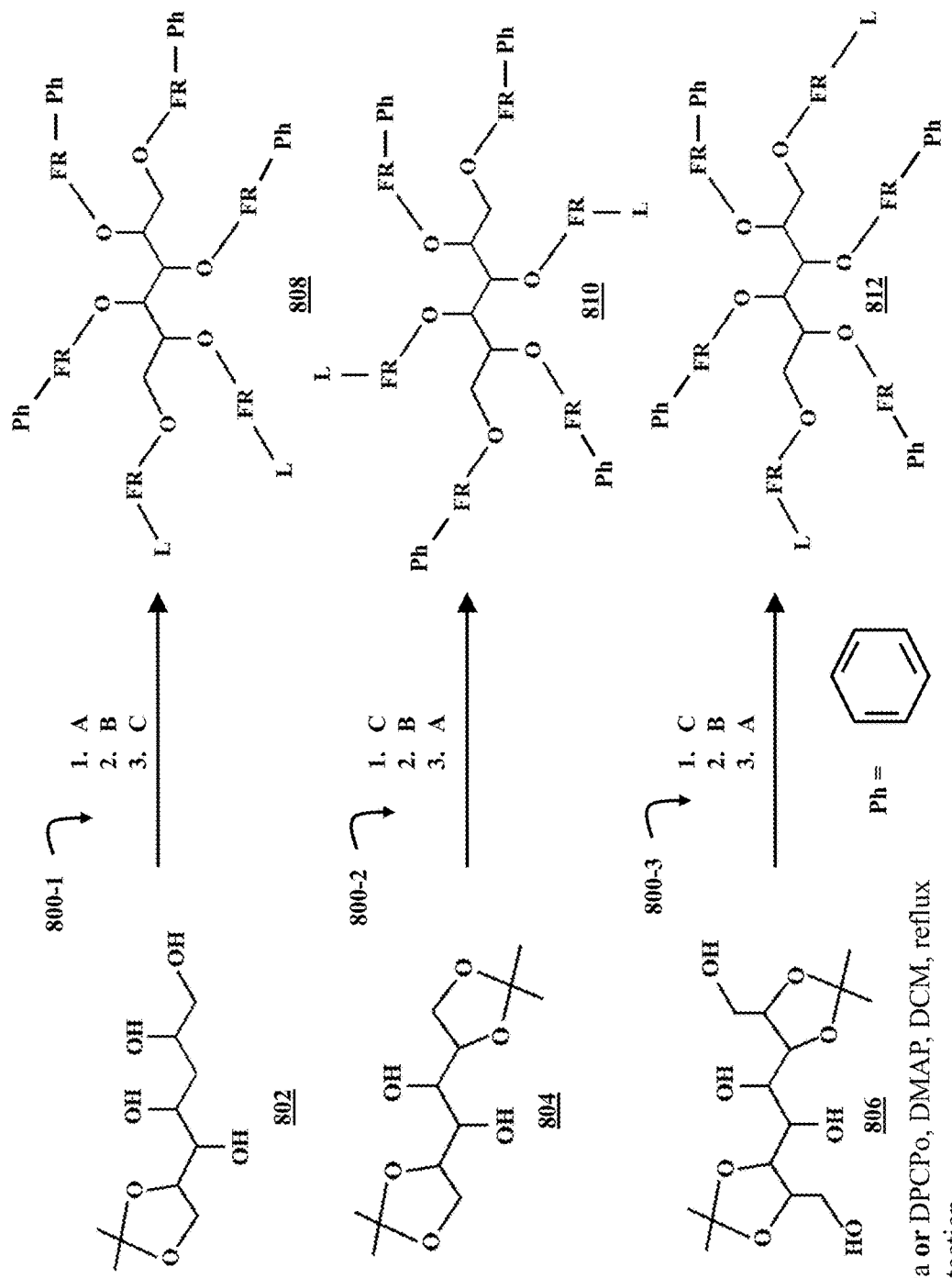
FIG. 8A is a chemical reaction diagram illustrating three processes synthesizing difunctionalized flame-retardant sorbitol derivatives, in accordance with embodiments of the present disclosure.

FIG. 8A is a chemical reaction diagram illustrating three processes 800-1, 800-2, and 800-3 of synthesizing difunctionalized flame-retardant sorbitol derivatives 808, 810, and 812, in accordance with embodiments of the present disclosure. In process 800-1, a terminal diprotected polyol 802 is reacted with either diphenyl chlorophosphate (DPCPa) or diphenylphosphinic chloride (DPCPo). The mixture is refluxed with catalytic dimethylaminopyridine (DMAP) in a dichloromethane (DCM) solution. Afterwards, the resulting molecule is deprotected and the hydroxyl groups are bound with functional linkers "L," producing a 1,2 difunctionalized flame-retardant sorbitol derivative 808. In process 800-2 the hydroxyl groups of a terminal tetraprotected polyol 804 are bound with functional linkers "L," and are then deprotected. After deprotection, the sorbitol derivative is reacted with either diphenyl chlorophosphate (DPCPa) or diphenylphosphinic chloride (DPCPo) and refluxed with catalytic dimethylaminopyridine (DMAP) in a dichloromethane (DCM) solution, yielding a 3,4 difunctionalized flame-retardant sorbitol derivative 810. In process 800-3, hydroxyl groups of an internal tetraprotected polyol 806 are bound with functional linkers "L." Afterwards, the resulting molecule is deprotected, and then reacted with either diphenyl chlorophosphate (DPCPa) or diphenylphosphinic chloride (DPCPo) and refluxed with catalytic dimethylaminopyridine (DMAP) in a dichloromethane (DCM) solution, yielding a 1,6 difunctionalized flame-retardant sorbitol derivative 812.

Figure 8B:
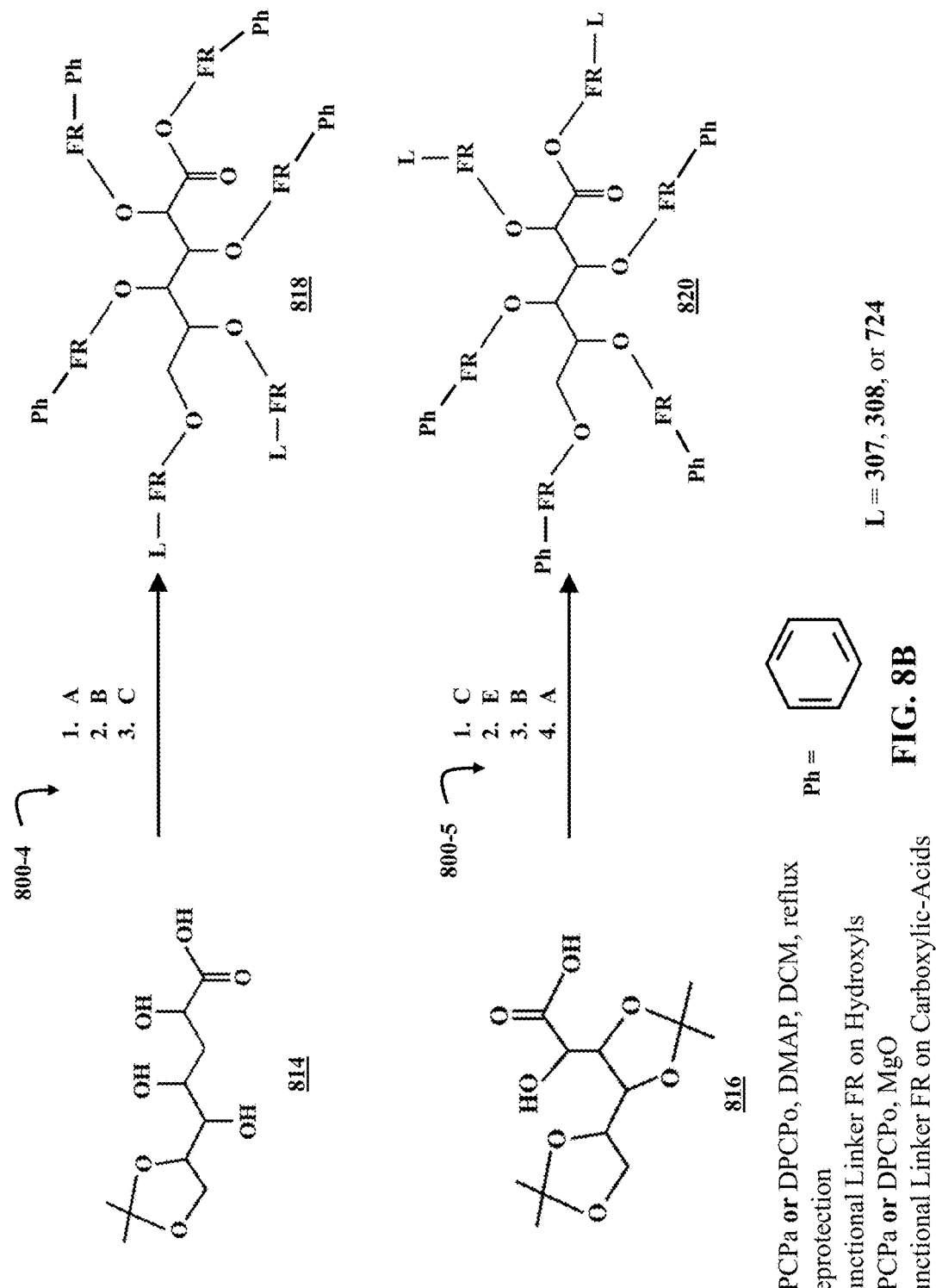
FIG. 8B is a chemical reaction diagram illustrating two processes of synthesizing difunctionalized flame-retardant gluconic acid derivatives, in accordance with embodiments of the present disclosure.

FIG. 8B is a chemical reaction diagram illustrating two processes 800-4 and 800-5 of synthesizing difunctionalized flame-retardant gluconic acid derivatives 818 and 820, in accordance with embodiments of the present disclosure. In process 800-4, a diprotected monoacid 814 is reacted with either diphenyl chlorophosphate (DPCPa) or diphenylphosphinic chloride (DPCPo). The mixture is refluxed with catalytic dimethylaminopyridine (DMAP) in a dichloromethane (DCM) solution. Afterwards, the resulting molecule is deprotected and the hydroxyl groups are bound with functional linkers "L," producing a 1,2 difunctionalized flame-retardant gluconic acid derivative 818. In process 800-5 the hydroxyl groups of a tetraprotected monoacid 816 are bound with functional linkers "L." Afterwards, the carboxylic acid groups of the resulting molecule are bound with functional linkers "L." The resulting molecule is then deprotected. After deprotection, the resulting molecule is reacted with either diphenyl chlorophosphate (DPCPa) or diphenylphosphinic chloride (DPCPo) and refluxed with catalytic dimethylaminopyridine (DMAP) in a dichloromethane (DCM) solution, yielding a 5,6 difunctionalized flame-retardant gluconic acid derivative 820.

Figure 8C:
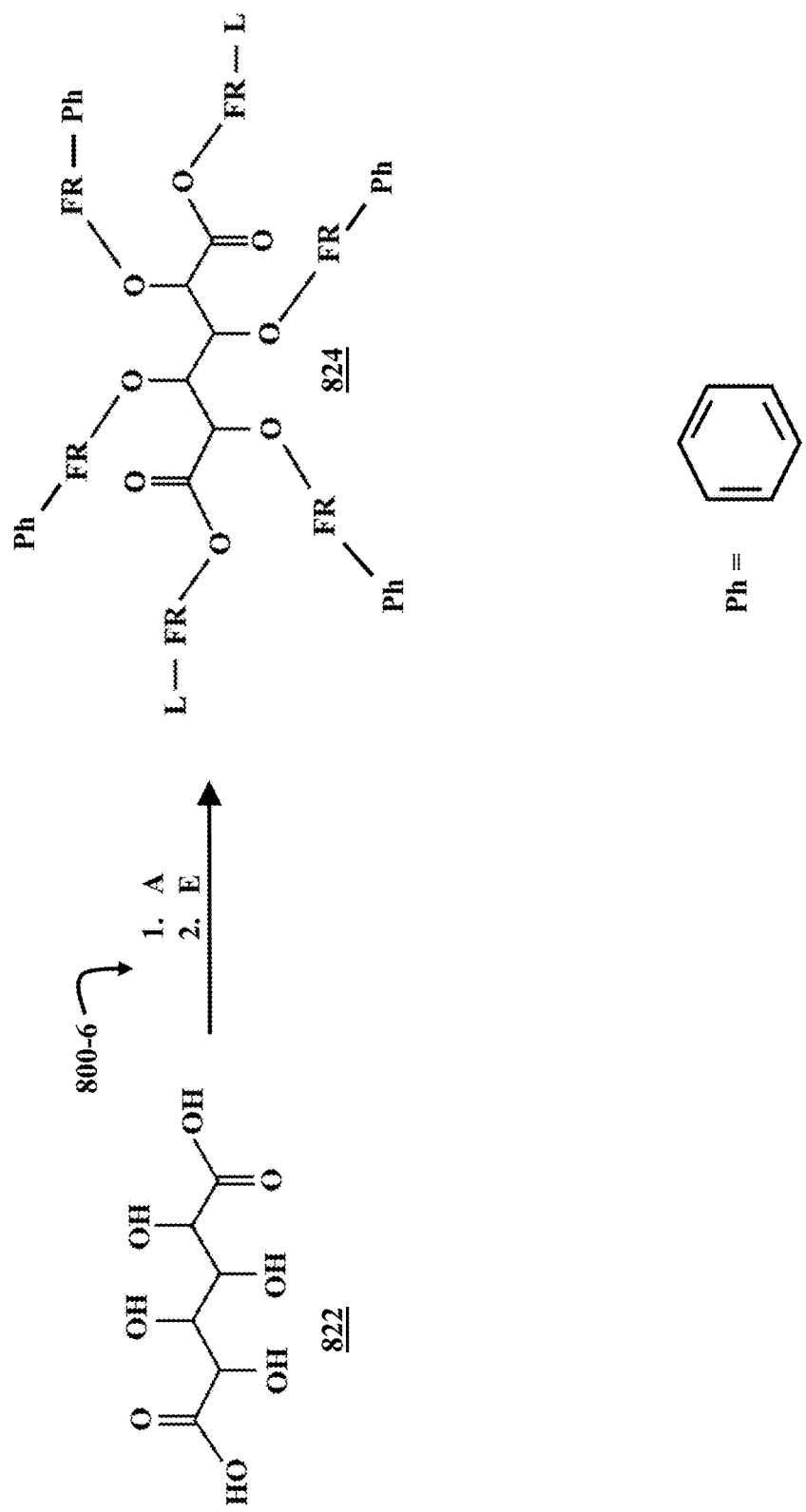
FIG. 8C is a chemical reaction diagram illustrating a process of synthesizing a 1,6 difunctionalized flame-retardant glucaric acid derivative, in accordance with embodiments of the present disclosure.

FIG. 8C is a chemical reaction diagram illustrating a process 800-6 of synthesizing a 1,6 difunctionalized flame-retardant glucaric acid derivative 824, in accordance with embodiments of the present disclosure. In process 800-6, glucaric acid 822 is reacted with either diphenyl chlorophosphate (DPCPa) or diphenylphosphinic chloride (DPCPo). The mixture is refluxed with catalytic dimethylaminopyridine (DMAP) in a dichloromethane (DCM) solution. Afterwards, the carboxylic acid groups are bound with functional linkers "L," producing a 1,6 difunctionalized flame-retardant glucaric acid derivative 824.

Figure 8D:
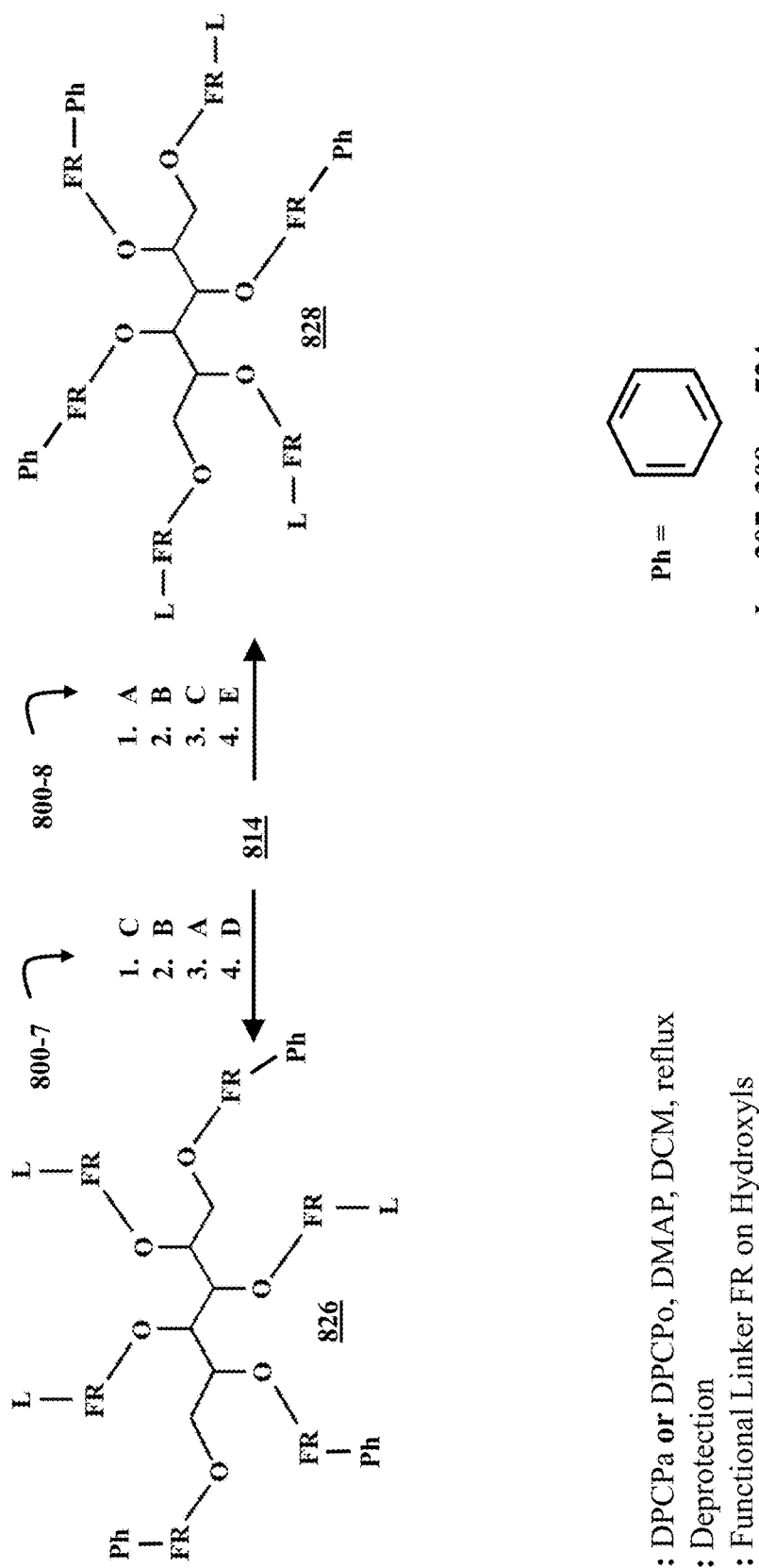
FIG. 8D is a chemical reaction diagram illustrating two processes of synthesizing trifunctionalized flame-retardant sorbitol derivatives, in accordance with embodiments of the present disclosure.

FIG. 8D is a chemical reaction diagram illustrating two processes 800-7 and 800-8 of synthesizing trifunctionalized flame-retardant sorbitol derivatives 826 and 828, in accordance with embodiments of the present disclosure. In process 800-7, hydroxyl groups of the diprotected monoacid 814 are bound with functional linkers "L." Afterwards, the resulting molecule is deprotected, and then reacted with either diphenyl chlorophosphate (DPCPa) or diphenylphosphinic chloride (DPCPo). The mixture is refluxed with catalytic dimethylaminopyridine (DMAP) in a dichloromethane (DCM) solution. Afterwards, the resulting molecule is reacted with either diphenyl chlorophosphate (DPCPa) or diphenylphosphinic chloride (DPCPo) in a magnesium oxide solution (MgO), yielding a 3,4,5 trifunctionalized flame-retardant sorbitol derivative 826. In process 800-7, the diprotected monoacid is reacted with either diphenyl chlorophosphate (DPCPa) or diphenylphosphinic chloride (DPCPo). The mixture is refluxed with catalytic dimethylaminopyridine (DMAP) in a dichloromethane (DCM) solution. Afterwards, the resulting molecule is deprotected. After deprotection, the hydroxyl groups are bound with functional linker "L," and the carboxylic acid groups are bound with functional linker "L," yielding a 1,2,6 trifunctionalized flame-retardant sorbitol derivative 828.

Figure 8E:
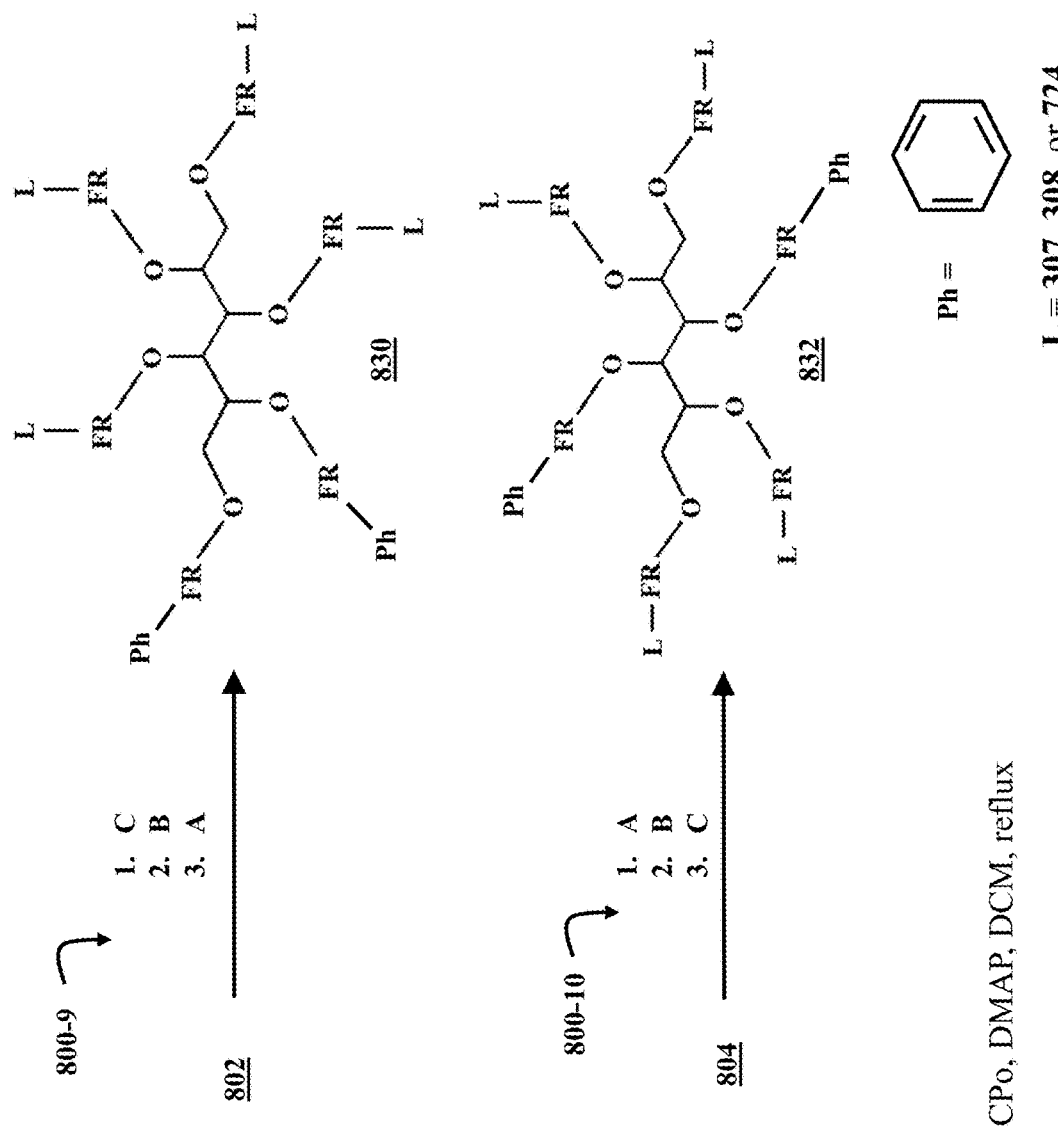
FIG. 8E is a chemical reaction diagram illustrating two processes of synthesizing tetrafunctionalized flame-retardant sorbitol derivatives, in accordance with embodiments of the present disclosure.

FIG. 8E is a chemical reaction diagram illustrating two processes 800-9 and 800-10 of synthesizing tetrafunctionalized flame-retardant sorbitol derivatives 830 and 832, in accordance with embodiments of the present disclosure. In process 800-9, hydroxyl groups of the terminal diprotected polyol 802 are bound with functional linkers "L." Afterwards, the resulting molecule is deprotected, and then reacted with either diphenyl chlorophosphate (DPCPa) or diphenylphosphinic chloride (DPCPo). The mixture is refluxed with catalytic dimethylaminopyridine (DMAP) in a dichloromethane (DCM) solution, yielding a 3,4,5,6 tetrafunctionalized flame-retardant sorbitol derivative 830. In process 800-10, the terminal diprotected polyol 802 is reacted with either diphenyl chlorophosphate (DPCPa) or diphenylphosphinic chloride (DPCPo). The mixture is refluxed with catalytic dimethylaminopyridine (DMAP) in a dichloromethane (DCM) solution. Afterwards, the resulting molecule is deprotected. After deprotection, the hydroxyl groups are bound with functional linker "L," yielding a 1,2,5,6 tetrafunctionalized flame-retardant sorbitol derivative 832.

Figure 8F:
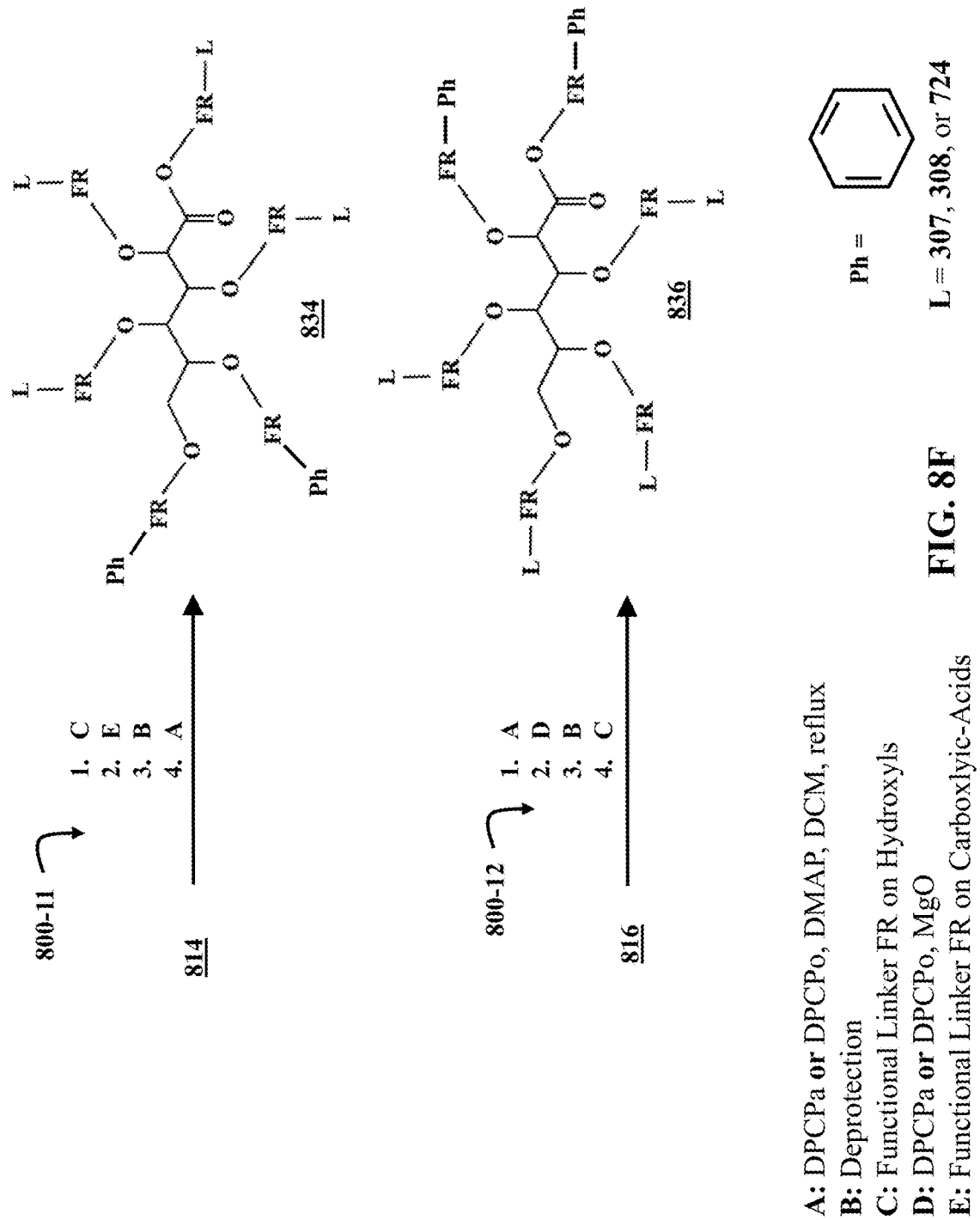
FIG. 8F is a chemical reaction diagram illustrating two processes of synthesizing tetrafunctionalized flame-retardant gluconic acid derivatives, in accordance with embodiments of the present disclosure.

FIG. 8F is a chemical reaction diagram illustrating two processes 800-11 and 800-12 of synthesizing tetrafunctionalized flame-retardant gluconic acid derivatives 834 and 836, in accordance with embodiments of the present disclosure. In process 800-11, hydroxyl groups of the diprotected monoacid 814 are bound with functional linkers "L," then carboxylic acid groups of the diprotected monoacid 814 are bound with functional linkers "L." Afterwards, the resulting molecule is deprotected, and then reacted with either diphenyl chlorophosphate (DPCPa) or diphenylphosphinic chloride (DPCPo). The mixture is refluxed with catalytic dimethylaminopyridine (DMAP) in a dichloromethane (DCM) solution, yielding a 3,4,5,6 tetrafunctionalized flame-retardant gluconic acid derivative 834. In process 800-12, the diprotected monoacid 816 is reacted with either diphenyl chlorophosphate (DPCPa) or diphenylphosphinic chloride (DPCPo). The mixture is refluxed with catalytic dimethylaminopyridine (DMAP) in a dichloromethane (DCM) solution. Afterwards, the resulting molecule is reacted with either diphenyl chlorophosphate (DPCPa) or diphenylphosphinic chloride (DPCPo) in a magnesium oxide (MgO) solution. Afterwards, the resulting molecule is deprotected. After deprotection, the hydroxyl groups are bound with functional linkers "L," yielding a 1,2,3,4 tetrafunctionalized flame-retardant gluconic acid derivative 836.

Figure 8G:
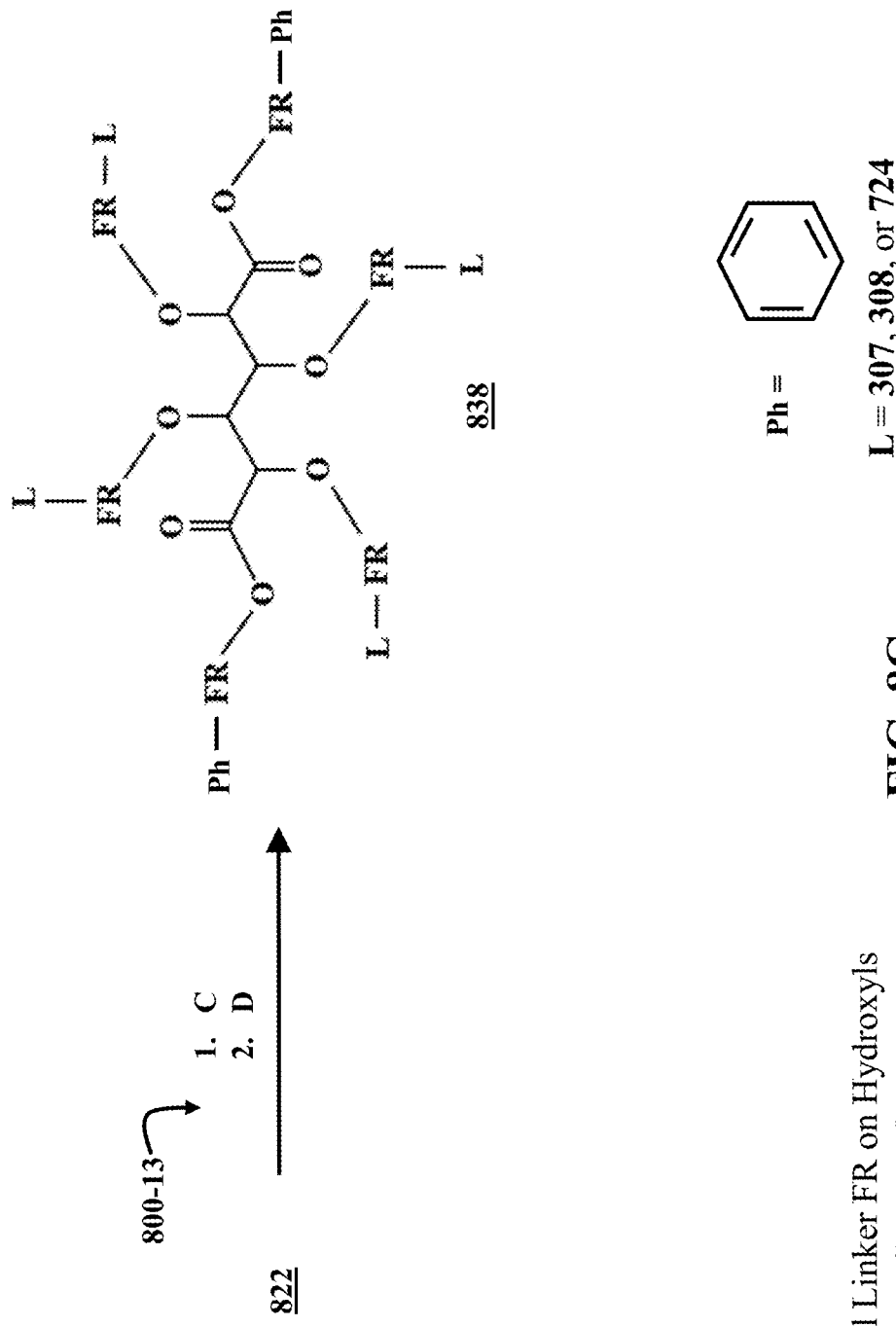
FIG. 8G is a chemical reaction diagram illustrating a process of synthesizing a 2,3,4,5-tetrafunctionalized flame-retardant glucaric acid derivative, in accordance with embodiments of the present disclosure.

FIG. 8G is a chemical reaction diagram illustrating a process 800-13 of synthesizing a 2,3,4,5 tetrafunctionalized flame-retardant glucaric acid derivative 838, in accordance with embodiments of the present disclosure. In process 800-13, hydroxyl groups of glucaric acid 822 are bound with functional linkers "L." Afterwards, the resulting molecule is reacted with either diphenyl chlorophosphate (DPCPa) or diphenylphosphinic chloride (DPCPo) in a magnesium oxide (MgO) solution yielding the 2,3,4,5 tetrafunctionalized flame-retardant glucaric acid derivative 838.

Figure 9:
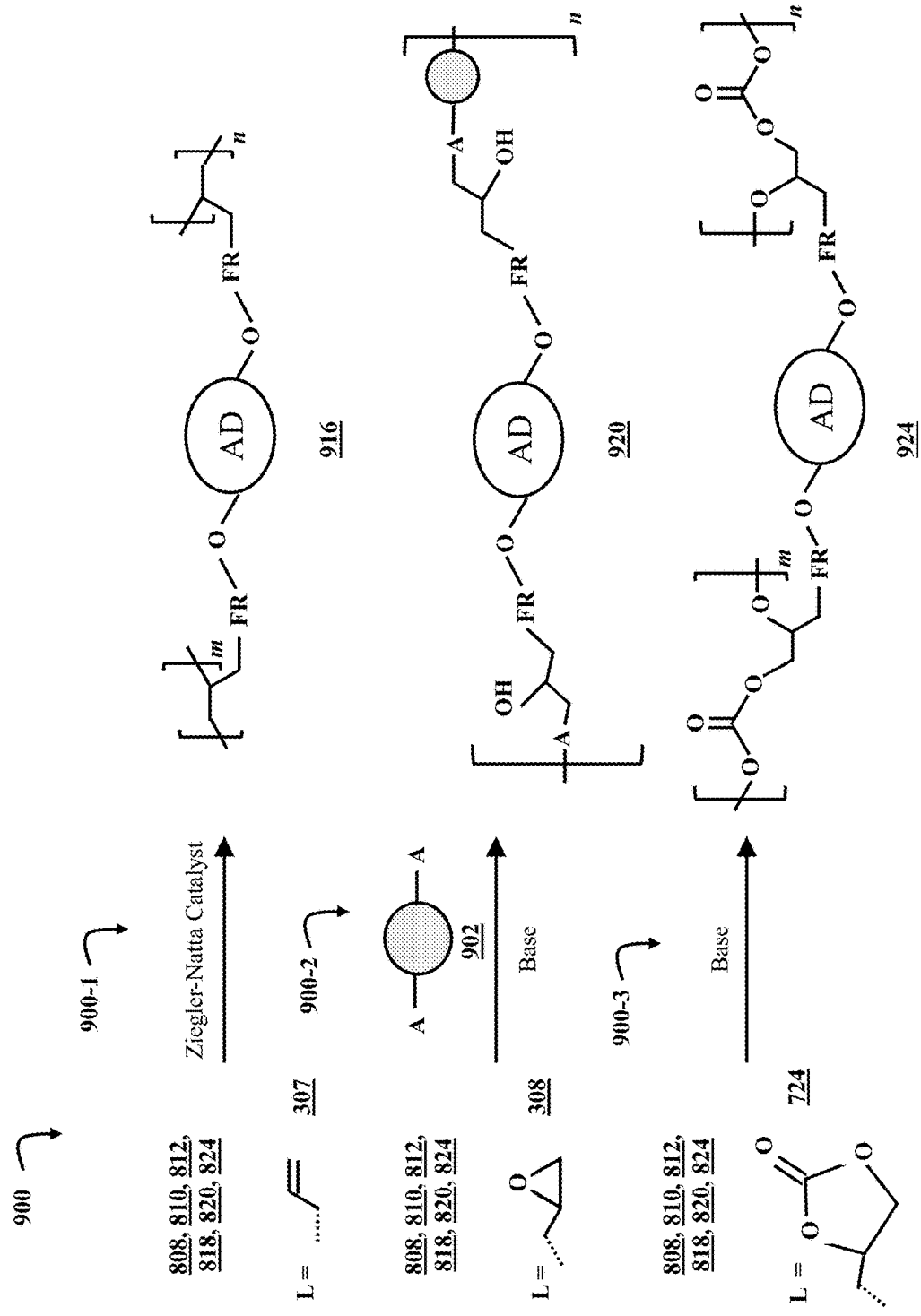
FIG. 9 is a chemical reaction diagram illustrating processes of synthesizing flame-retardant sorbitol-based gluconic acid-based or glucaric acid-based polymers from flame-retardant sorbitol-derived, gluconic acid-derived, or glucaric acid-derived monomers, in accordance with embodiments of the present disclosure.

FIG. 9 is a chemical reaction diagram illustrating processes 900 of synthesizing flame-retardant sorbitol-based, gluconic acid-based, or glucaric acid-based polymers 916, 920, and 924 from flame-retardant sorbitol-derived, gluconic acid-derived, or glucaric acid-derived monomers, in accordance with embodiments of the present disclosure. The reactions illustrated herein are prophetic examples of polymers that can be synthesized from the flame-retardant sorbitol-derived, gluconic acid-derived, or glucaric acid-derived monomers, but other polymers can be produced as well (e.g., by changing reaction conditions, co-monomers, R groups, etc.).

Processes 900-1, 900-2, and 900-3 illustrate the polymerization of difunctionalized flame-retardant sorbitol-derivatives, gluconic acid-derivatives, or glucaric acid-derivatives 808, 810, 812, 818, 820, and 824 only. However, it should be noted that each of these polymerization reactions can also be carried out with the trifunctionalized flame-retardant sorbitol derivatives (e.g., 826 and 828), tetrafunctionalized flame-retardant sorbitol derivatives, gluconic acid derivatives, or glucaric acid derivatives (e.g., 830, 832, 834, 836, or 838), pentafunctionalized flame-retardant gluconic acid derivatives, and/or hexafunctionalized sorbitol derivatives, gluconic acid derivatives, or glucaric acid derivatives (e.g., 520, 540, 726 and 728, also referred to as cross-linkers). Further, processes 900-1 and 900-3 may similarly be carried out with monofunctionalized flame-retardant gluconic acid derivatives (e.g., 604 and 610).

In some embodiments, the polymerization reactions are carried out with a combination of mono, di, tri, tetra, penta, and/or hexa monomers. Any combination of monomers (e.g., mono and di, mono and tetra, di and hexa, tri and penta, etc.) may be polymerized. Further, any ratio of monomers may be combined.

In process 900-1, allyl-derived flame-retardant sorbitol, gluconic acid, or glucaric acid based polymers 916 are formed from diallyl-functionalized flame-retardant sorbitol-derivatives, gluconic acid-derivatives, or glucaric acid-derivatives 808, 810, 812, 818, 820, or 824, where L=307. The diallyl-functionalized flame-retardant sorbitol-derivative, gluconic acid-derivative, or glucaric acid-derivative 808, 810, 812, 818, 820, or 824 is reacted with a Ziegler-Natta catalyst. Ziegler-Natta catalysts catalyze the polymerization of 1-alkenes. Examples of these catalysts can include heterogeneous Ziegler-Natta catalysts based on titanium compounds and homogeneous Ziegler-Natta catalysts based on complexes of titanium, zirconium, or hafnium. Heterogeneous and homogeneous Ziegler-Natta catalysts can be used in combination with organoaluminum co-catalysts in some embodiments.

In process 900-2, epoxy-derived flame-retardant sorbitol, gluconic acid, or glucaric acid based polymers 920 are formed from diepoxy functionalized flame-retardant sorbitol-derivatives, gluconic acid-derivatives, or glucaric acid-derivatives 808, 810, 812, 818, 820, or 824, where L=308. The diepoxy-functionalized flame-retardant sorbitol-derivative, gluconic acid-derivative, or glucaric acid-derivative 808, 810, 812, 818, 820, or 824 is reacted with a base and a second monomer 902. The second monomer 902 is a compound with at least two hydroxyl (OH) groups or at least two amino ($NH_2$) groups (e.g., a diol, polyol, diamine, polyamine, etc.) 902. These compounds 902 are illustrated as a gray oval with attached A groups. The A group represents a hydroxyl group or an amino group. It should be noted that, while two A groups are illustrated herein, there are more than two A groups in some embodiments. Additionally, in some embodiments, the diepoxy-functionalized sorbitol-derivative, gluconic acid-derivative, or glucaric acid-derivative 808, 810, 812, 818, 820, or 824 self-polymerizes under basic conditions. In these instances, the reaction does not include the second monomer 902.

In process 900-3, propylene carbonate-derived flame-retardant sorbitol, gluconic acid, or glucaric acid based polymers 924 are formed from dipropylene carbonate-functionalized flame-retardant sorbitol-derivatives, gluconic acid-derivatives, or glucaric acid-derivatives 808, 810, 812, 818, 820, and 824, where L=724. The dipropylene carbonate-functionalized flame-retardant sorbitol-derivative, gluconic acid-derivative, or glucaric acid-derivative 808, 810, 812, 818, 820, or 824 is reacted in a ring-opening polymerization initiated by a base. Examples of bases that can be used as initiators can include potassium hydroxide (KOH), sodium hydroxide (NaOH), lithium hydroxide (LiOH), etc.

In addition to the polymers illustrated in FIG. 9, the flame-retardant sorbitol-derivatives, gluconic acid-derivatives, or glucaric acid-derivatives disclosed herein can be used in the synthesis of other flame-retardant polymers, in some embodiments. An array of classes of flame-retardant polymers can be made with different combinations of monomers. These polymerization processes are in accordance with polymer chemistry platforms that can include polyhydroxyurethanes, polycarbonates, polymers obtained by radical polymerization, polyurethanes, polyesters, polyacrylates, polycarbonates, epoxy resins, polyimides, polyureas, polyamides, poly(vinyl-esters), etc.

One example of an application of polymers made, at least in part, from flame-retardant sorbitol-derivatives, gluconic acid-derivatives, or glucaric acid-derivatives is in plastics used in electronics hardware. Additional applications can include acoustic dampening, cushioning, plastics, synthetic fibers, insulation, etc. The flame-retardant sorbitol-derivatives, gluconic acid-derivatives, or glucaric acid-derivatives can also be used to make adhesives such as bio-adhesives, elastomers, thermoplastics, emulsions, thermosets, etc. Further, materials containing the flame-retardant sorbitol-derivatives, gluconic acid-derivatives, or glucaric acid-derivatives can be incorporated into various devices with electronic components that can include printed circuit boards (PCBs), semiconductors, transistors, optoelectronics, capacitors, resistors, etc.

Resins for printed circuit boards (PCBs) can be made flame-retardant by incorporating polymers that are made, at least in part, from sorbitol-derivatives, gluconic acid-derivatives, or glucaric acid-derivatives. PCBs are electrical circuits that can be found in most types of electronic device, and they support and electronically connect electrical components in the device. PCBs are formed by etching a copper conductive layer laminated onto an insulating substrate. The insulating substrate can be a laminate comprising a resin and a fiber. Many resins in PCBs contain a polymer, such as an epoxy, a polyhydroxyurethane, a polycarbonate, a polyester, a polyacrylate, a polyimide, a polyamide, a polyurea, a poly(vinyl-ester), etc. Using polymers that incorporate the flame-retardant sorbitol-derivatives, gluconic acid-derivatives, or glucaric acid-derivatives can prevent the PCB from catching fire when exposed to high temperature environments or electrical power overloads.

It should be noted that, in some embodiments, the compounds described herein can contain one or more chiral centers. These can include racemic mixtures, diastereomers, enantiomers, and mixtures containing one or more stereoisomer. Further, the disclosed can encompass racemic forms of the compounds in addition to individual stereoisomers, as well as mixtures containing any of these.

The synthetic processes discussed herein and their accompanying drawings are prophetic examples, and are not limiting; they can vary in reaction conditions, components, methods, etc. In addition, the reaction conditions can optionally be changed over the course of a process. Further, in some embodiments, processes can be added or omitted while still remaining within the scope of the disclosure, as will be understood by a person of ordinary skill in the art.

What is claimed is:

1. A flame-retardant sugar derivative with a formula of:

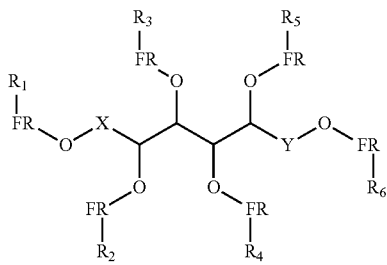

wherein X is selected from a group consisting of a methanediyl moiety and a carbonyl moiety;
wherein Y is selected from the group consisting of the methanediyl moiety and the carbonyl moiety;
wherein FR is a phosphorus-based moiety;
wherein $R_1$ is a substituent selected from a group consisting of an allyl substituent, an epoxide substituent, a propylene carbonate substituent, a phenyl substituent, and a thioether substituent;
wherein $R_2$ is a substituent selected from a group consisting of an allyl substituent, an epoxide substituent, a propylene carbonate substituent, a phenyl substituent, and a thioether substituent;
wherein $R_3$ is a substituent selected from a group consisting of an allyl substituent, an epoxide substituent, a propylene carbonate substituent, a phenyl substituent, and a thioether substituent;
wherein $R_4$ is a substituent selected from a group consisting of an allyl substituent, an epoxide substituent, a propylene carbonate substituent, a phenyl substituent, and a thioether substituent;
wherein $R_5$ is a substituent selected from a group consisting of an allyl substituent, an epoxide substituent, a propylene carbonate substituent, a phenyl substituent, and a thioether substituent;
wherein $R_6$ is a substituent selected from a group consisting of an allyl substituent, an epoxide substituent, a propylene carbonate substituent, a phenyl substituent, and a thioether substituent.

2. The flame-retardant sugar derivative of claim 1, wherein the FR is a phosphoryl moiety with a formula of:

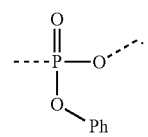

3. The flame-retardant sugar derivative of claim 1, wherein the FR is a phosphonyl moiety with a formula of:

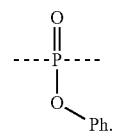

4. The flame-retardant sugar derivative of claim 1, wherein $R_1$ is a phenyl substituent, wherein $R_2$ is a phenyl substituent, wherein $R_3$ is a phenyl substituent, wherein $R_4$ is a phenyl substituent, wherein $R_5$ is a phenyl substituent, and wherein $R_6$ is a phenyl substituent.

5. The flame-retardant sugar derivative of claim 1, wherein $R_1$ is an epoxide substituent, wherein $R_2$ is epoxide substituent, wherein $R_3$ is an epoxide substituent, wherein $R_4$ is an epoxide substituent, wherein $R_5$ is an epoxide substituent, and wherein $R_6$ is an epoxide substituent.

6. The flame-retardant sugar derivative of claim 1, wherein $R_1$ is an allyl substituent, wherein $R_2$ is allyl substituent, wherein $R_3$ is an allyl substituent, wherein $R_4$ is an allyl substituent, wherein $R_5$ is an allyl substituent, and wherein $R_6$ is an allyl substituent.

7. The flame-retardant sugar derivative of claim 1, wherein $R_1$ is a propylene carbonate substituent, wherein $R_2$ is a propylene carbonate substituent, wherein $R_3$ is a propylene carbonate substituent, wherein $R_4$ is a propylene carbonate substituent, wherein $R_5$ is a propylene carbonate substituent, and wherein $R_6$ is a propylene carbonate substituent.

8. The flame-retardant sugar derivative of claim 1, wherein the thioether substituent is selected from a group consisting of a hydroxyl-functionalized thioether substituent, an amino-functionalized thioether substituent, and a carboxylic acid-functionalized thioether substituent.

9. The flame-retardant sugar derivative of claim 1, wherein X is a methanediyl moiety, wherein Y is a carbonyl moiety, wherein $R_1$ is a phenyl substituent, wherein $R_2$ is a phenyl substituent, wherein $R_3$ is a phenyl substituent, wherein $R_4$ is a phenyl substituent, wherein $R_5$ is a phenyl substituent, and wherein $R_6$ is not a phenyl substituent.

10. The flame-retardant sugar derivative of claim 1, wherein X is a methanediyl moiety, wherein Y is a carbonyl moiety, wherein $R_1$ is not a phenyl substituent, wherein $R_2$ is not a phenyl substituent, wherein $R_3$ is not a phenyl substituent, wherein $R_4$ is not a phenyl substituent, wherein $R_5$ is not phenyl substituent, and wherein $R_6$ is a phenyl substituent.

11. The flame-retardant sugar derivative of claim 1, wherein the flame-retardant sugar-derived molecule is selected from a group of difunctionalized flame-retardant sugar-derived molecules with formulas of:

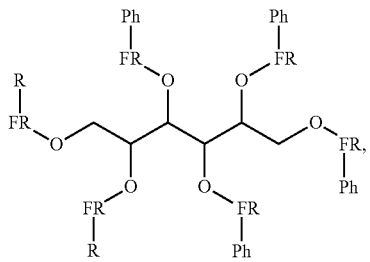

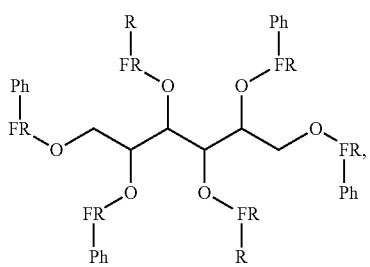

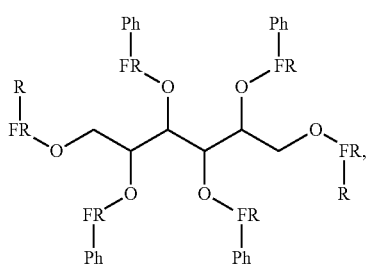

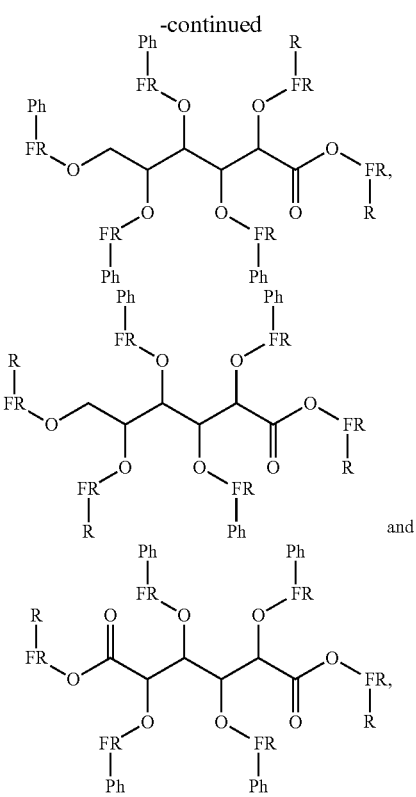

wherein R is a functional group selected from a group consisting of the allyl functional group, the epoxy functional group, and the propylene carbonate functional group; and wherein Ph is the phenyl substituent.

12. The flame-retardant sugar derivative of claim 1, wherein the flame-retardant sugar-derived molecule is selected from a group of trifunctionalized flame-retardant sugar-derived molecules with formulas of:

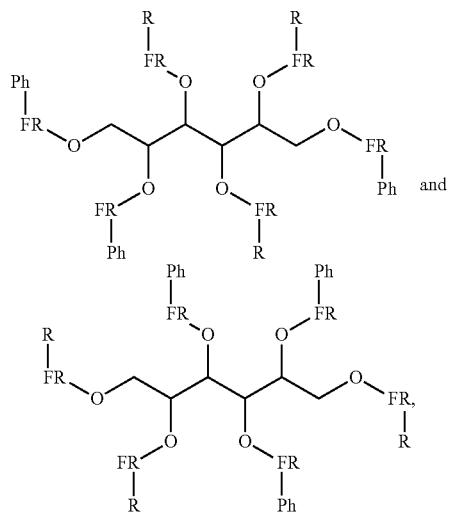

wherein R is a functional group selected from a group consisting of the allyl functional group, the epoxy functional group, and the propylene carbonate functional group; and wherein Ph is the phenyl substituent.

13. The flame-retardant sugar derivative of claim 1, wherein the flame-retardant sugar-derived molecule is selected from a group of tetrafunctionalized flame-retardant sugar-derived molecules with formulas of:

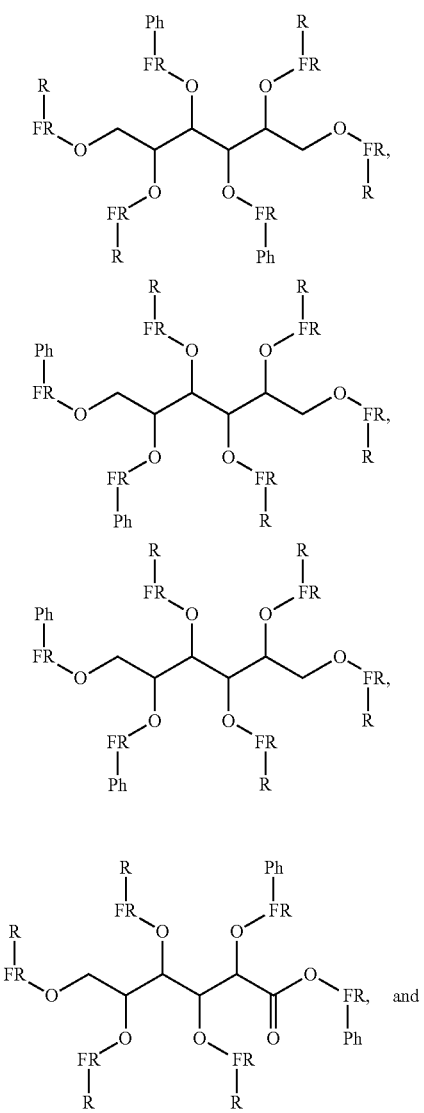

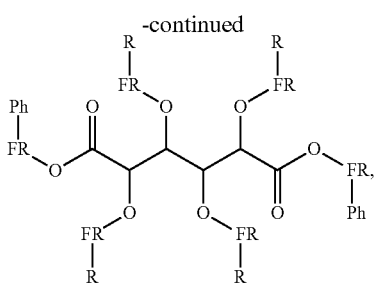

wherein R is a functional group selected from a group consisting of the allyl functional group, the epoxy functional group, and the propylene carbonate functional group; and wherein Ph is the phenyl substituent.

14. A method of forming a flame-retardant polymer, comprising:
obtaining a phosphorus-based flame-retardant molecule;
obtaining a sugar derivative;
chemically reacting the sugar derivative with the phosphorus-based flame-retardant molecule to form the flame-retardant sugar derivative according to claim 1; and
processing the functionalized flame-retardant sugar derivative into a polymer.

15. The method of claim 14, wherein processing the flame-retardant sugar derivative into the polymer includes at least one of blending and binding the flame-retardant sugar derivative with the polymer to form the flame-retardant polymer.

16. The method of claim 14, wherein processing the flame-retardant sugar derivative into the polymer includes polymerizing the flame-retardant sugar derivative to form the flame-retardant polymer.

17. An article of manufacture, comprising a material containing the flame-retardant sugar derivative according to claim 1.

18. The article of manufacture of claim 17, wherein the material is selected from a group consisting of an adhesive, a resin, and a polymer.

19. The article of manufacture of claim 17, wherein the material is selected from a group consisting of polyurethane, an epoxy, a polyhydroxyurethane, a polycarbonate, a polyester, a polyacrylate, a polyimide, a polyamide, a polyurea, and a poly(vinyl-ester).

20. The article of manufacture of claim 17, further comprising a printed circuit board.

* * * * *